United States Patent [19]
Rosenfeld et al.

[11] Patent Number: 5,484,732
[45] Date of Patent: Jan. 16, 1996

[54] TRANSCRIPTION FACTOR FOR REGULATION OF THE DEVELOPMENT OF SKIN AND HAIR

[75] Inventors: Michael G. Rosenfeld, San Diego; Bogi Anderson, La Jolla, both of Calif.

[73] Assignee: The Regents of the University of California, Oakland, Calif.

[21] Appl. No.: 35,392

[22] Filed: Mar. 22, 1993

[51] Int. Cl.$^6$ .......................... C12N 15/11; C12N 15/12; C12N 15/63; C07K 14/00
[52] U.S. Cl. .................. 435/320.1; 530/350; 536/23.5; 930/10; 935/9; 935/18; 935/19; 935/21; 935/23
[58] Field of Search ............................... 536/23.1, 23.5; 435/240.1, 240.2, 69.1, 252.3, 320.1

[56] References Cited

PUBLICATIONS

A. Goldsborough et al (1990) 18 (6): 1634.
A. Goldsborough et al (1993) 21 (1): 127–134.

*Primary Examiner*—Jacqueline M. Stone
*Assistant Examiner*—Johnny F. Railey, II
*Attorney, Agent, or Firm*—Fish & Richardson

[57] ABSTRACT

A gene encoding for alternative forms of a POU domain transcription factor is disclosed. The first polypeptide form of the transcription factor includes a transferable region which inhibits DNA binding by itself and other transcription factors. The second polypeptide form serves to activate expression of a gene typical for terminal differentiation of skin. Fusion proteins wherein the inhibitory region of the first form of the gene is coupled to, and inhibits the function of, other transcription factors are also disclosed.

28 Claims, 18 Drawing Sheets

FIG. 2(A)

EXHIBIT 3(a)

```
rSKN-1a    1   MVNLEPMLSEIKMSGDVADSTDARSTFGQVESGNDRNGLDFNRQIKTEDLGDT         53
rSKN-1a        LHESLSHRPCHLTEGPTMMPGNQMSGDMASLHPLQQLVLVPGHLQSVSQFLLSQTPPGQQG  114
               IR rSKN-1i    1   MSVMFSLSFKWPGFCLFVCLFLCPFVLPCHSG                              32
hOCT-2    58   PSTKIKAEDPSGDSAPAAPLPPQPAQPHLPQAQLMLTGSQLAGDIQQLLQLQQLVLVPGHH 144 rSKN-1a/i      LQPNLLSFPQQQSTLLLPQTGPGLTSQAVGRPGLSGSSLEPHLEASQ              161/79
hOCT-2         LQPPAQFLLPQAQQSQPGLLPTPNLFQLPQQTQGALLTSQPRAGLPTQAVTRPTLPDPHLS 184

POU SPECIFIC DOMAIN rSKN-1a/i      HLPGPKHLPGPGPGGNDEPTDLEELEKFAKTFKQRRIKLGFTQGDVGLAMGKLYGNDFSQTTI  222/140
hOCT-2         HPQPPKCLEPPSHPEEPSDLEELEQFARTFKQRRIKGFTQGDVGLAMGKLYGNDFSQTTI  245
```

FIG. 2(B)

```
                LINKER
rSKN-1a/i       SRFEALNLSFKNMCKLKPLLEKWLNDAESSPADPSASTPSSYPTLSEVFGRKKRKKRT    279/197
hOCT-2          SRFEALNLSFKNMCKLKPLLEKWLNDAETMSVDSSLPSPNQLSSPSLGFDGLPGRRRKKRT    306

POU HOMEODOMAIN
rSKN-1a/i       SIETNIRLTLEKRFQDNPKPSSEEISMIAEQLSMEKEVVRVRVWFCNRRQKEKRINCPVATPV    340/258
hOCT-2          SIETNVRFEALEKSFLANQKPTSEEILLIAEQLHMEKEVIRVWFCNRRQKEKRINPCSAAPM    367 rSKN-1a/i       KPPIYNSRLVSPSGSLGSLSVPPVHSTMPGTVTSSCSPGNNSRPS                     385/303
hOCT-2          LPSPGKPASYSPHMVTPQGGAGTLPLSQASSSLSTTVTTLSSAVGTLHPSRTAGGGGGGGG    428 rSKN-1a/i       SPGSGLHASSPTASQNNSKAAMNPSSAAFNSSGSWYRWNHPAYLH                     430/348
hOCT-2          AAPPLNSIPSVTPPPPATTNSTNPSPQGSHSAIGLSGLNPSTGPGLWWNPAPYQP           484
```

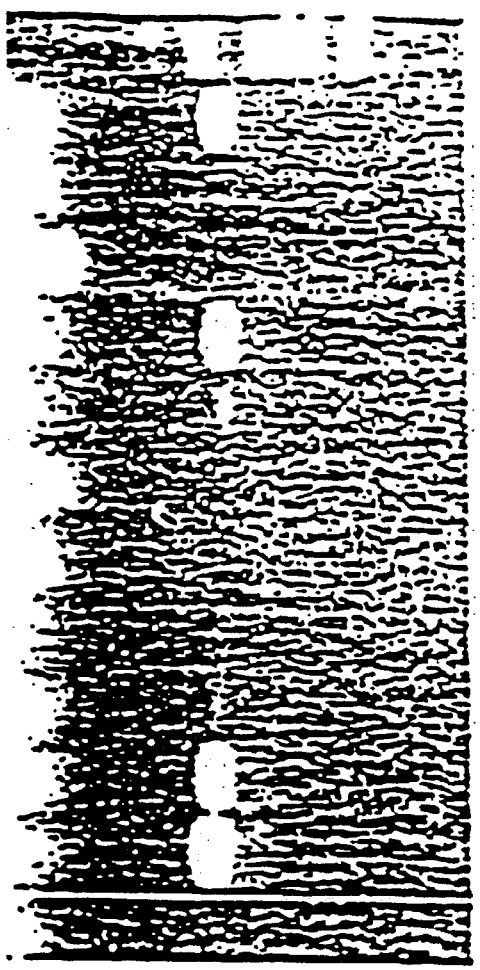
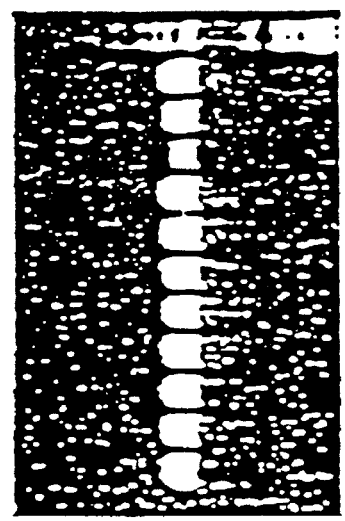
FIG. 3

FIG. 16

| LCR | Skn-1a | E6 | E7 | EXPRESSION LEVELS |
|---|---|---|---|---|
| + | – | – | – | 1 |
| + | + | – | – | 7.46 |
| + | – | + | – | 0.49 |
| + | – | + | + | 0.50 |
| + | + | + | – | 92.38 |
| + | + | + | + | 107.73 |
| + | + | + | + | 97.47 |

TRANSCRIPTION FACTOR FOR REGULATION OF THE DEVELOPMENT OF SKIN AND HAIR

STATEMENT OF GOVERNMENT RIGHTS

This invention was made with Government support under Grant No. DK-18477, awarded by the National Institute of Health. The Government has certain rights in this invention.

BACKGROUND OF THE INVENTION

1. Field of the Invention

This invention relates to the POU domain family of transcriptional regulators (named after three of the earliest identified members of this family: Pit-1, Oct-1 and unc-86). More specifically, it relates to a novel POU domain gene which alternatively and selectively expresses at least two forms of a protein in terminally differentiating epidermal cells and hair follicles. The first expressed form of the gene contains a region which inhibits DNA binding by itself and other transcription factors. The second form apparently serves as a transcriptional activator of, for example, cytokeratin 10 (K10) and human papilloma virus-1 (HPV-1) gene expression in skin. The gene expresses proteins which vary in sequence and length at their amino termini.

2. Description of Related Art

The POU domain family of tissue-specific transcription factors express proteins having two conserved domains: a C-terminal homeodomain of approximately 60 amino acids and an N-terminal POU specific domain of approximately 81 amino acids, which domains are connected by a variable linker region. The homeodomain is a DNA binding domain which has been found to play a central role in eukaryotic gene regulation; in general, the POU specific domain enhances the affinity of POU domain proteins for certain target DNA binding sites and may also be involved in protein-protein interactions.

The first three mammalian POU domain transcription factors (Oct-1, Oct-2 and Pit-1) were characterized and described in 1988 (see, Ingraham, et al. (1988) *Cell*, 55: 519–529; Bodner, et al. (1988) *Cell.*, 55:508–518; and, Ko et al (1988) *Cell*, 55:135–144). Thereafter, a strategy was described for identifying and isolating additional members, if any, of the POU domain family using the polymerase chain reaction (PCR) and degenerate oligonucleotides representing all possible codons for two 9-amino-acid residues conserved among Oct-1, Oct-2, Pit-1 and a C. elegans regulatory gene product, unc-86 (see, He, et al. (1989) *Nature* 340:35–42). Following this technique, POU domain genes have been isolated from a variety of organisms and show diverse patterns of expression. Proteins encoded by POU domain genes include several which bind to a specific octamer DNA motif (5'-ATGCAAAT-3'), which is believed to be required for ubiquitous and tissue-specific expression of various genes. These proteins (commonly known as Oct-1 through Oct-10 in the mouse and by alternative names in humans) have generally been found to be present in embryonic and adult tissue in the mouse and humans as follows:

| Oct Proteins | Synonyms | Gene | EXPRESSION Embryo | Adult |
| --- | --- | --- | --- | --- |
| Oct-1 | Human: OTF-1; NF-A1 NF-III; OBP 100 | Oct-1 (1) | Ubiquitous | Ubiquitous |
| Oct-2 | Human: OTF-2; NF-A2 N-Oct_ | Oct-2 (7) | Neural tube; in entire brain except telencephalon | Lymphoid cells; nervous system; intestine; testis; kidney |
| N-Oct-2 | Human: N-Oct_ | — | Nervous system | Nervous system (Astrocytes, certain glioblastoma and neuralblastoma cell lines) |
| MiniOct-2 | — | Oct-2 (7) | Nervous system (strong expression in developing nasal neuroepithelium) | Nervous system primary spermatids |
| N-Oct-3 | — | — | Nervous system | Nervous system (certain glioblastoma and neuroblastoma cell lines) |
| Oct-4A | NF-A3; Oct-3 | Oct-4 (17) | Totipotent and pluripotent stem cells of the pregastrulation embryo, embryonic ectoderm, primodial germ cells; testis, ovary | Oocytes |
| Oct-4B | — | | | |
| Oct-5 | — | | | |
| Oct-6 | Rat: Tst-1; SCIP | Oct-6 (4) | Blastocyst; ES and EC cells; brain | Nervous system testis |
| Oct-7 | Human: N-Oct-4 | — | Nervous system | Nervous system |
| Oct-8 | Human: | — | Nervous system | Nervous system (astrocytes) |
| Oct-9 | N-Oct5a | | | |
| Oct-10 | N-Oct5b | | | |

Although the above list should not be regarded as exhaustive, it serves to demonstrate the predominance of many members of this gene family in orchestrating precise temporal and spatial expression of genes during development of the neural system (particularly the forebrain), endocrine system and, for Oct-4 and Oct-6, embryonic and adult reproductive tissues.

Consistent with this expected distribution, part of the POU domain of an eleventh Oct gene was identified as being present (but not functional) in mouse testis by PCR and a proposed partial sequence of the gene published in 1990 (Goldsborough, et al. (1990) *Nuc. Acids. Res* 18:1634). Although not prior art, it is notable that more recent (1993) data published by these same authors led them to the conclusion that this eleventh gene (referred to as "Oct-11") is expressed in a tissue-specific manner during mouse embryogenesis and in adult thymus and testis tissue as well as myeloma cell line P3/NS-1/1-Ag4.1. However, the authors also concluded that only one form of the gene was present in rats and humans and only one active form was present in the mouse genome.

The results reported by Goldsborough, et al. did not predict or suggest either that quantity of expression of the "Oct-11" gene or its potential function. Their results regarding the distribution of the Oct-11 transcript (as reported in the 1990 *Nuc. Acids. Res.* article) were necessarily limited by the sensitive, nonquantitative nature of the PCR methods used. Specifically, as known in the art, the use of PCR to identify genes suggested in the 1989 He, et al. *Nature* article will amplify DNA expressed from genes present in tissues even in minute quantities, regardless of whether a function is served by the gene in the source tissue. Therefore, while helpful in identifying the existence of potentially new genes, the PCR approach used by Goldsborough, et al. does not reveal patterns of expression or function for identified genes (see, e.g., Raffle, et al. (1992) *Science* 257:1118–1121, reporting the presence of Pit-1 [which is only functional in the pituitary] in lymphcid cells).

In contrast, based on data developed prior to the 1993 publication by Goldsborough, et al., and contrary to their conclusions therein, not only are two functional forms of an eleventh Oct gene expressed in both rats and humans, the genes are not limited in their distribution to testis and thymus tissue or the P3/NS-1/1Ag4.1 cell line. Instead, alternative full-length forms of these genes (hereafter respectively referred to as "Skn-1*a*" and "Skn-1*i*") are selectively expressed in terminally differentiating epidermal cells and hair follicles. In this context, distinct regions of Skn-1a/i play functional roles in regulating skin development.

For perspective, it should be considered that while skin is the largest organ in mature mammals, cell-specific transcription factors involved in epidermal cell maturation have been previously unknown (although several factors of wide distribution are known to be expressed in skin, including AP2, retionic acid receptor γ and retinoid X receptor α). Therefore, an understanding of the role of Skn-1i/a in epidermal cell development may be facilitated by a brief illustration of the pattern of this development in the rat.

Epidermal development in the rat does not begin until embryonic days (e) 15 to 16. Before this stage, the primordium of epidermis consists of a bilayer of cells, a superficial layer referred to as periderm that is later shed and a basal layer. On e 16, the basal cells begin to proliferate, generating a stratified epithelium in which a characteristic subset of genes (such as keratins) are differentially regulated within each layer. Most of the suprabasal epidermal cells are post-mitotic, and eventually undergo programmed cell death, generating a superficial layer of dead cells (cornified epithelium) that appears on e 18. This pattern of development, in which cells migrate to the surface during their differentiation only to undergo apoptosis, is continuously repeated in the adult, where the process is regulated by retinoic acid.

Skn-1i and Skn-1 a's roles in this process appear, at least in part, to respectively be in the specific inhibition of DNA binding by transcription factors (particularly the ubiquitous Oct-1 protein) and in the control of this inhibitory activity by Skn-1 a. Ultimately, controlled expression of these genes may not only lead to further insight into the regulation of skin development but may also assist in the clinical control of skin cell proliferation for use in, for example, regenerating skin and terminating metastasis of tumor cells.

SUMMARY OF THE INVENTION

The details of the preferred embodiment of the present invention are set forth in the accompanying drawings and the description below. Once the details of the invention are known, numerous additional innovations and changes will become obvious to one skilled in the art.

A full-length cDNA clone has been isolated from rat skin cells from neonatal tissues. The clone has been sequenced and shown to predict a 38 kDa protein that is highly related to the Oct-2 transcription factor. Consistent with that relationship, the POU domain of this protein binds the 5'-ATGCAAAT-3' octamer which is bound with high affinity by Oct-1 and Oct-2. That DNA binding activity is, however, inhibited by a 21–32 amino acid sequence at the amino terminus of the Skn-1i form of the expressed protein. This inhibitory region is transferable to other classes of DNA binding proteins and can prevent DNA binding not only by Skn-1i, but also specifically inhibits transcriptional activation by Oct-1.

The Skn-1 a gene expresses a protein which differs from Skn-1i by a 113 amino acid sequence which replaces the initial 31 residues of Skn-1i at the amino terminus. This form of the gene is capable of binding DNA (at the POU domain) and positively regulating transcription by activation of expression.

Expression of the Skn-1i/a gene is specific in skin to identifiable stages of cell proliferation corresponding to development and maturation of the epidermis as well as cyclical hair growth. Both forms of the gene have been shown to be present in rats; sequence homology among POU domain proteins and the presence of these proteins in human keratinocytes would also predict patterns of expression and function for the gene in humans and other mammals similar to those found in the rat and mouse.

BRIEF DESCRIPTION OF THE DRAWINGS AND SEQUENCES

FIG. 2 is a copy of the amino acid sequences (SEQ ID No. 2 and No. 4) predicted, respectively, by the full-length Skn-1i/a cDNA clones wherein boxes are placed to show complete sequence identity between Skn-1i/a and the Oct-2 protein, with gaps introduced for maximal alignment.

FIG. 3 depicts the results of polymerase chain reaction analysis of Skn-1i/a mRNA expression in the developing mouse embryo.

FIG. 16 depicts the results of transient transfection assays of the indicated expression plasmids in HeLa cells.

DETAILED DESCRIPTION OF THE INVENTION

A. Skn-1i Gene Sequence and Patterns of Expression

SEQ ID No:1 and SEQ ID No:3 are respectively the nucleotide sequences of the full-length cDNA's for Skn-1i/a. These clones were isolated and identified from a number of tissues as follows.

Polyadenylated RNA was isolated from rat embryonic head; e 15, e 19 and adult anterior rat pituitary; adult kidney; medullary thyroid tumor (WG), mouse thyrotroph tumor (Tt97), and corticoid cell line ATt-20 by means of the MICRO FAST TRACK kit from Invitrogen of San Diego, Calif. cDNA's were synthesized using random hexamers and SUPERSCRIPT reverse transcriptase from Bethesda Research Laboratory (commercially available) according to the vendor's instructions.

The POU domain fragments obtained through PCR included Oct-1 and Oct-2. These fragments were $^{32}$P-labeled and used in combination to screen approximately 500,000 plaques from a rat pituitary cDNA library under low stringency. Using this approach two clones were obtained, Oct-1 and a 2192 base pair (bp) long cDNA (SEQ ID No: 1).

Both strands of the 2192 bp SEQ ID No:1 Skn-1a clone were sequenced by the dideoxy nucleotide replication method described by Sanger et al. (see, e.g., Sanger, et al. (1977) *Proc. Natl. Acad. Sci. U.S.A.* 7: 5463) and by use of the SEQUENASE Version 2.0 Kit [a DNA polymerase 1 product available from USB of Cleveland, Ohio]). The clone contains a single open reading frame of 1044 bp in addition to a 277 bp untranslated sequence at the 5' terminus and a 873 bp untranslated sequence at the 3' terminus. A detailed description regarding the isolation and sequencing of the Skn-1a clone [SEQ ID No:3] may be found at Section D, below.

The conclusion that SEQ ID No:1 and SEQ ID No:3 represent full-length clones is supported by data in at least two respects. First, there are stops in the reading frame upstream of the initiating methionine the latter of which is at nucleotide 279 in SEQ ID No:1 and at 46 in SEQ ID No:3. Second, as to Skn-1i, there is good agreement between the size of the Skn-1i cDNA and the size of RNA transcript (2.3 kb) as determined by Northern blot analysis performed according to the basic protocol described in Ausubel, et al., *Current Protocols in Molecular Biology* (Greene Publishing and Wiley-Interscience, 1989), Vol. I, Unit 4.9).

Figure 1:
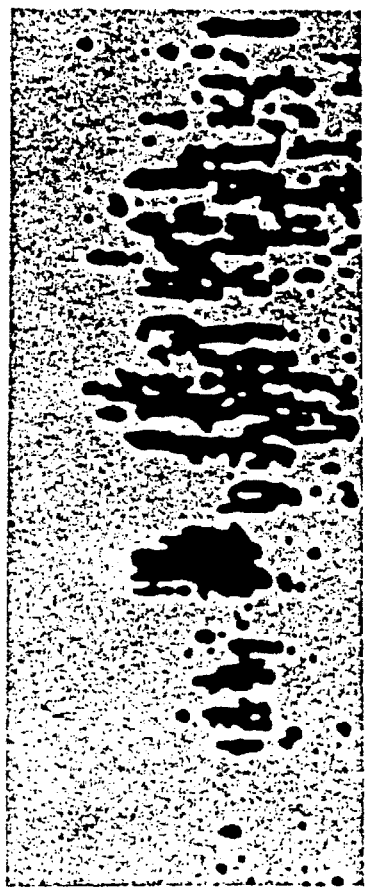
FIG. 1 depicts the results of a Northern blot analysis showing the size of the RNA transcript of the clone of SEQ ID No:1 (Skn-1i) to be 2.3 kb.

The marker ladder depicting the results of this analysis is shown in FIG. 1; the ladder was purchased commercially from Bethesda Research Laboratory. The transcript itself was isolated from neonatal mouse tissues according to the methods described in Chomczynski, et al. (1987) *Anal. Biochem* 162:156–159. SEQ ID No:2 and SEQ ID No:4 are the predicted amino acid sequences for Skn-1i and Skn-1a cDNA. The POU homeodomain and POU specific domains are identified in FIG. 2, as is the intervening linker region. The non-conserved inhibitory region of Skn-1i ("IR") is identified by the presence of a black bar over the region.

Further in FIG. 2, each of these regions of Skn-1i/a is compared with amino acids 58 to 480 (counting from the amino terminus) of the human Oct-2 protein (also commonly referred to as OTF-2 and NF-A2). Sequence identity is shown by boxed regions; gaps have been introduced for maximal alignment. In the POU domains, Skn-1i/a differ from Oct-2 by only 15 amino acids, although there is greater variation in the linker regions of Oct-2 and Skn-1i/a and between the IR region of Skn-1i and a corresponding region in Oct-2. As discussed further herein, this high degree of conservation in between Oct-2 and Skn-1i POU domains suggests the existence of an alternative DNA binding form, which has been identified as Skn-1a.

To evaluate the pattern of expression of the Skn-1i/a gene during development, mouse embryos were collected from the blastocyst stage through e 16.5. These embryos and blastocysts were isolated by standard techniques as described by Hogan, et al. *Manipulating the Mouse Embryo:A Laboratory Manual* (Cold Spring Harbor Laboratory, 1986), the disclosure of which is incorporated herein by this reference. From these tissues, polyadenylated RNA was isolated using the MICRO FAST TRACK kit sold by Invitrogen of San Diego, Calif., cDNA's were synthesized SUPERSCRIPT reverse transcriptase and random hexamers.

The resulting cDNA was used as a PCR template and the reaction was performed using the following primers, selected for specificity to mouse Skn-1i POU domains (sense: 5'-TAAAGCTTG TTGAATGATGCAGATCCTC-CCG-3'; antisense: 5'-ATGGATCCCACCACCTCCT-TCTCCATCGAT-3') or for β actin (sense: 5'-GATCGAAT-TCGACGAGGCGCAGAGCAAGAGAGG-3'; antisense: 5'-GATCGGATCCCTCTTTGATGTCACGCACGATITC-3'). These primers flanked introns in the template to avoid priming by genomic DNA. The primers specific for Skn-1i/a were used to amplify a 236 bp POU domain fragment (corresponding for Skn-1i to amino acids 273 to 350 of SEQ ID No:2. A 477 bp fragment known in the art to be specific for β actin (not shown) was also amplified as a control using the described oligonucleotide primers.

Referring to FIG. 3, the results of this analysis (performed on 2% agarose gel) are shown. The DNA ladder used is commercially available from Bethesda Research Laboratory. P/E refers to Skn-1i/a expression in placental tissue and endometrium; My refers to cDNA's expression in myometrium; B refers to expression in blastocysts and the remainder of the panel depicts expression at indicated alares of embryonic development.

This analysis revealed a biphasic pattern of expression; a signal was detected on e 7.5, was low or undetectable between e 9.5 and e 12.5, but appeared again on e 14.5. In addition, an intense signal was observed in the P/E panel.

To expand this analysis using in-situ hybridization, rat embryos were immersion-fixed in 10% buffered formalin and 10–30 μm thick frozen sections were cut therefrom in a cryostat. Using $^{35}$S-labeled cRNA probes transcribed from plasmid vectors containing specific RNA synthesis promoters which vectors are commercially available from Promega (Madison, Wis.), and Stratagene (La Jolla, Calif.) as described by Simmons, et al. in *J. Histochem* (1989) 12:169–181 (the disclosure of which is incorporated herein by this reference), in-situ hybridizations were performed using an antisense probe corresponding to 5' untranslated sequence and the beginning of the coding region (nucleotides 1-279 of SEQ ID No:1) and another corresponding to the 3' untranslated region (nucleotides 1475 to 2192 of SEQ ID No:3). After hybridization, slides were dipped in NTB-2 liquid autoradiography emulsion (available from Kodak) and exposed for 5 to 7 days.

This analysis revealed no hybridization in rat embryos corresponding to the early phase of expression. However, there was intense hybridization at e 17 in epidermal structures throughout the embryo, most particularly at the epidermis ("E" in FIG. 4) and epidermal-mucosal junction ("M" in FIG. 4). No specific detectable hybridization was found in any other region; silver grains in the region of the heart, liver and brain in FIG. 4 result from non-specific adherence to red blood cells and edges, a conclusion borne out by the lack of Skn-1i/a mRNA found in rat embryo brain and liver tissue in polymerase chain reaction-reverse transcriptase (PCR-RT) analyses (results not shown).

Figure 4:
FIG. 4 depicts a darkfield photograph of a rat embryo following in-situ hybridization analysis for expression of Skn-1i/a mRNA therein.
Figure 5:
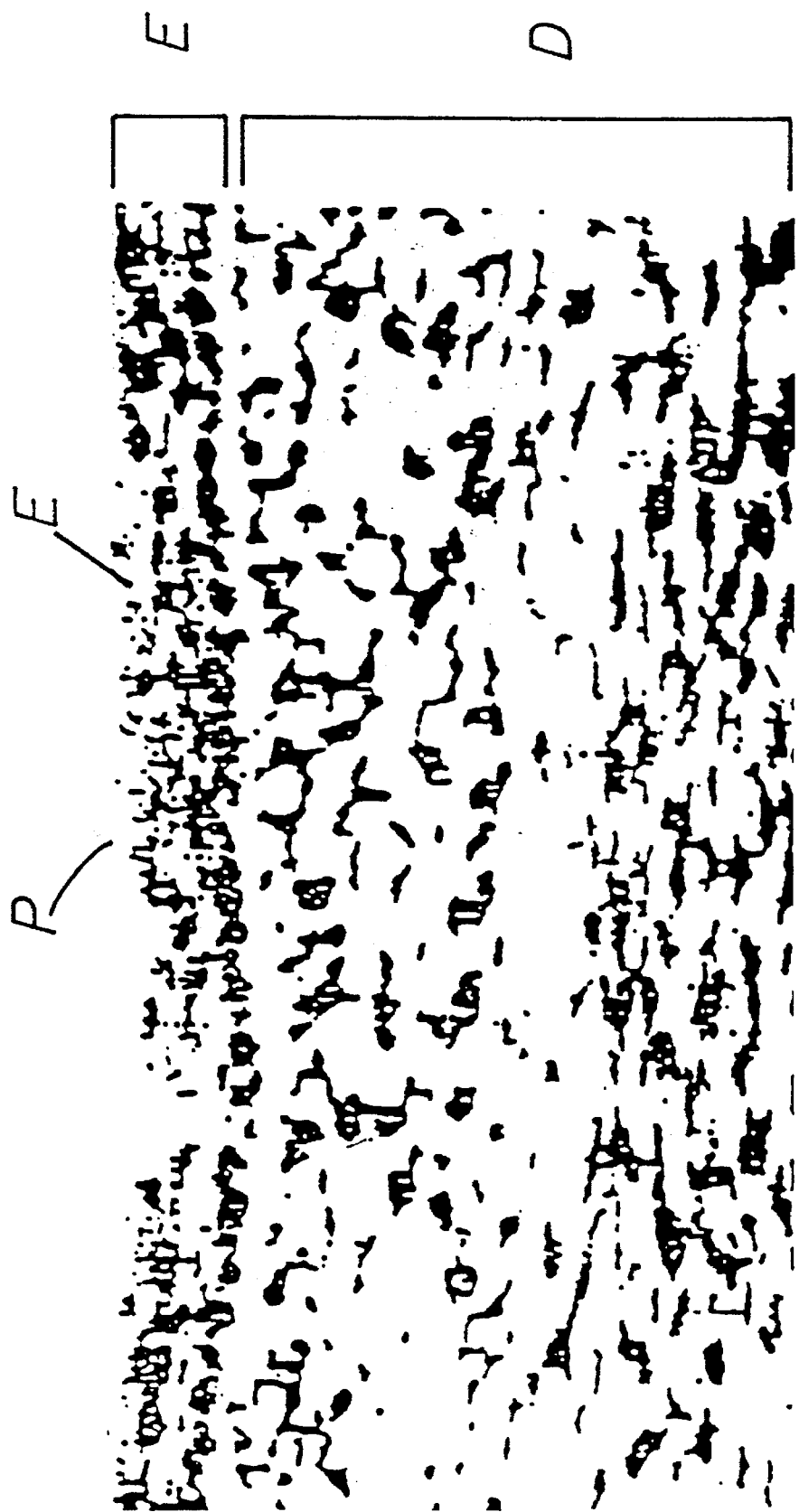
FIG. 5 is a lightfield photograph showing highly magnified skin cells from an e 17 rat embryo following the in-situ hybridization demonstrated in FIG. 4.

FIG. 5 is a higher resolution photograph of FIG. 4 revealing hybridization over the epidermis (E) but not the dermis (D), with the most intense hybridization occurring in the most superficial level of the epidermis. The periderm (P) is a single layer which showed no hybridization.

To identify areas where the Skn-1i/f gene is present, a sensitive RNase protection assay was performed which revealed expression in adult epidermis, but not in adult skeletal muscle, tongue, esophagus, heart, thymus, spleen, liver, kidney, testis, adrenals, placenta, lungs, brain and anterior pituitary of mice and rats. This assay was performed according to the protocol described in *Current Protocols in Molecular Biology*, Supra at Unit 4.7. Notably, the assay results showing no expression of the Skn-1i/a gene in mouse testis and thymus is at odds with Goldsborough, et al.'s 1993 report of expression of the gene referred to as Oct-11 (having a similar sequence) in tissues taken from these organs using PCR. These apparently contradictory results can be harmonized by considering the quantities of the partially sequenced "Oct-11" gene in thymus and testis to be relatively low and thus detectable by PCR but not RNase protection assay.

Figure 6:
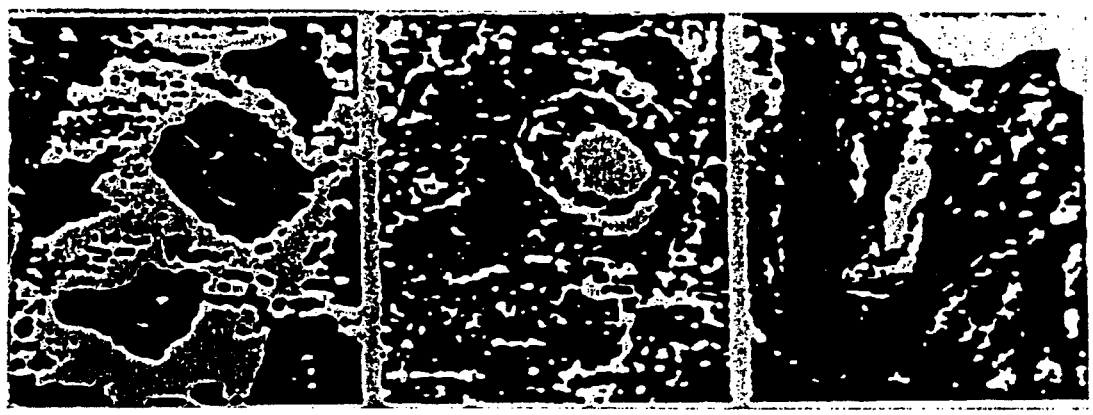
FIG. 6 depicts the results of in-situ hybridization analyses of Skn-1i/a mRNA expression in adult rat skin.

The RNase protection assay results with respect to expression in the epidermis are confirmed by in-situ hybridization analysis using adult rat skin and the method reported by Simmons, et al. in *J. Histochem*, supra. The results of this analysis are depicted in FIG. 6. In FIG. 6, the left (lightfield) and middle (darkfield) panels show high magnification of hair follicles. The arrow in each of these two panels show points of intense hybridization in the cortex cells of each follicle. Specific hybridization is also shown in suprabasal epidermal cells shown in the right (lightfield) panel, which is a photograph of epidermis at the entry point of hair. Hybridization is demonstrated by silver grains, identified by an arrow. The pattern of expression demonstrated in these panels is consistent with stage-specific expression during cyclical hair growth as described in Hardy (1992) *Trends in Genetics* 8:55–60.

B. Octamer Binding By the Skn-1i Protein

5'-ATGCAAAT-3' is a DNA octamer sequence which the Oct-1 and Oct-2 proteins are known to bind with high affinity (see, e.g., Baumruker, et al. (1988) *Genes and Dev.* 2:1400–1413 and Poellinger, et al. (1989) *Mol. Cell. Biol.* 9:747–746). However, despite the degree of sequence homology in the POU domains between these proteins and Skn-1i, the latter was unable to effectively bind to this octamer site.

Specifically, the full-length Skn-1icDNA was generated using PCR as described above. The full-length nucleotide sequence was then cloned into a T7 expression vector containing methionine for initiation in vitro, which expression vector has been described by Drolet, et al. in *Genes and Dev.* (1991) 5:1739, the disclosure of which is incorporated herein by reference. The Skn-1i protein was then synthesized in vitro in the presence of $^{35}$[S]-methionine using nuclease treated rabbit reticulocyte lysate.

The methods used to express the Skn-1i clone in the T7 expression vector are alternatively described in instruction manuals for in vitro translation kits sold by Stratagene of La Jolla, Calif. and Promega of Madison, Wis. The latter method is a single-step method for DNA isolation, generation of RNA and expression and is, therefore, preferred for its convenience. The Stratagene method is performed using its mCAP (trademarked name) mRNA capping kit for RNA synthesis and its IN VITRO TRANSLATION kit for expression. These products and their instruction manuals are, respectively, available from Stratagene's Catalog numbers 200350 and 200360. The Promega method is performed using its TNT T7 Coupled Reticulocyte Lysate System from its Catalog No. L4610, using as instructions its related technical Bulletin No. 126.

For comparison, a truncated form of the protein lacking the first 60 amino acids of the amino terminus, another lacking the carboxyl terminus (leaving amino acids 1 to 250 in place) and another lacking the entire amino terminus (leaving amino acids 100 to 348 in place) were synthesized in the same manner as described above with respect to Skn-1i or by using convenient restriction sites to advantage. All of the $^{35}$[S] labeled synthesized proteins were quantitated by trichloroacetic acid (TCA) precipitation and gel electrophoresis on SDS/polyacrylamide gels according to means well known in the art to ensure that equal amounts of each were used in each binding reaction.

Using 0.5 to 2 μl of programmed lysate, gel-mobility shift assays were performed as described by Yu, et al. in *Cell* 67:1251 (1991), except that binding reactions without probe were preincubated for 20 minutes on ice. Binding affinity was evaluated for the octamer-heptamer, Pr1-1P and POU domain binding sites whose sequences have been recently reported by one of the inventors and Mathias, et al. in *EMBO J.* 7:2551 (1992).

Figure 7:
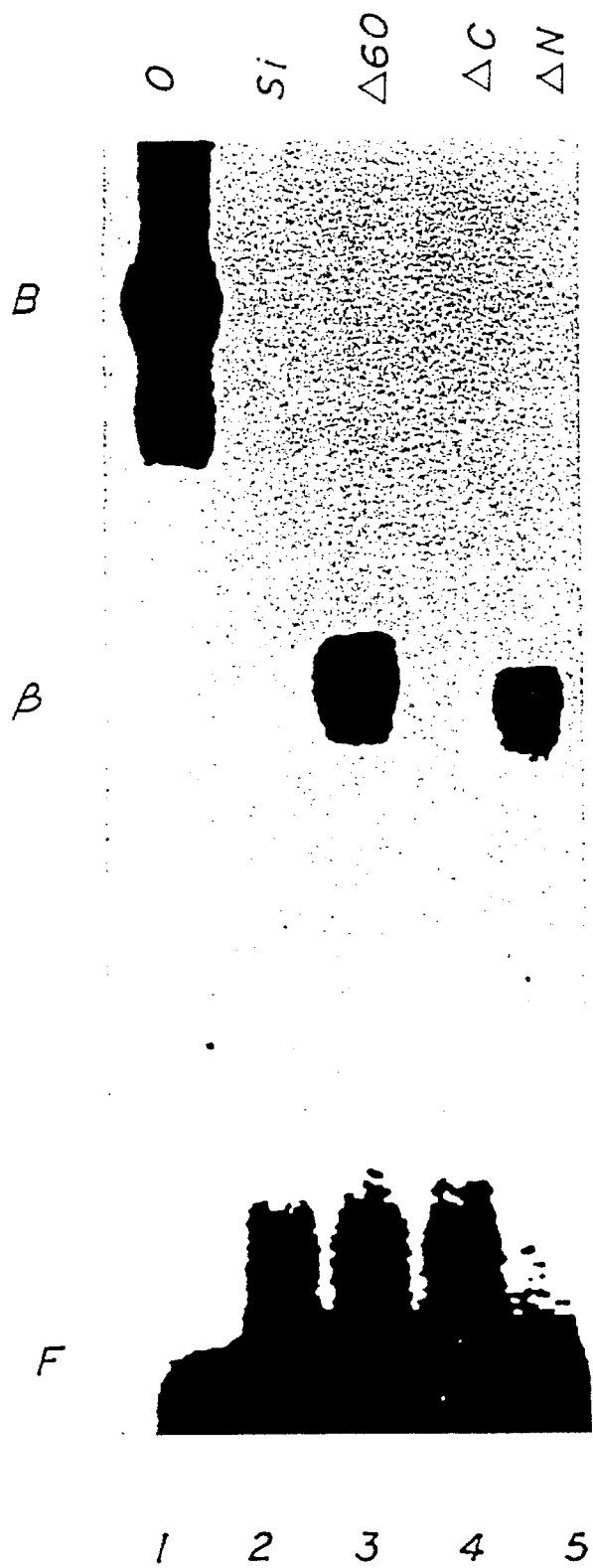
FIG. 7 depicts the results of a gel-mobility shift assay of Skn-1i with various modifications of its amino terminus.

FIG. 7 depicts the results of this assay for binding to the octamer-heptamer (Oct-Hep) site. Along the top axis, O refers to Oct-2 (as a control), Si refers to the in vitro Skn-1i protein; Δ60 refers to the Skn-1i protein without the first 60 amino acids from the amino terminus; ΔC refers to the protein without its carboxyl terminus; and ΔN refers to the protein without its amino terminus. The position of bound and free probes are indicated, respectively, by "B" and "F".

Figure 8:
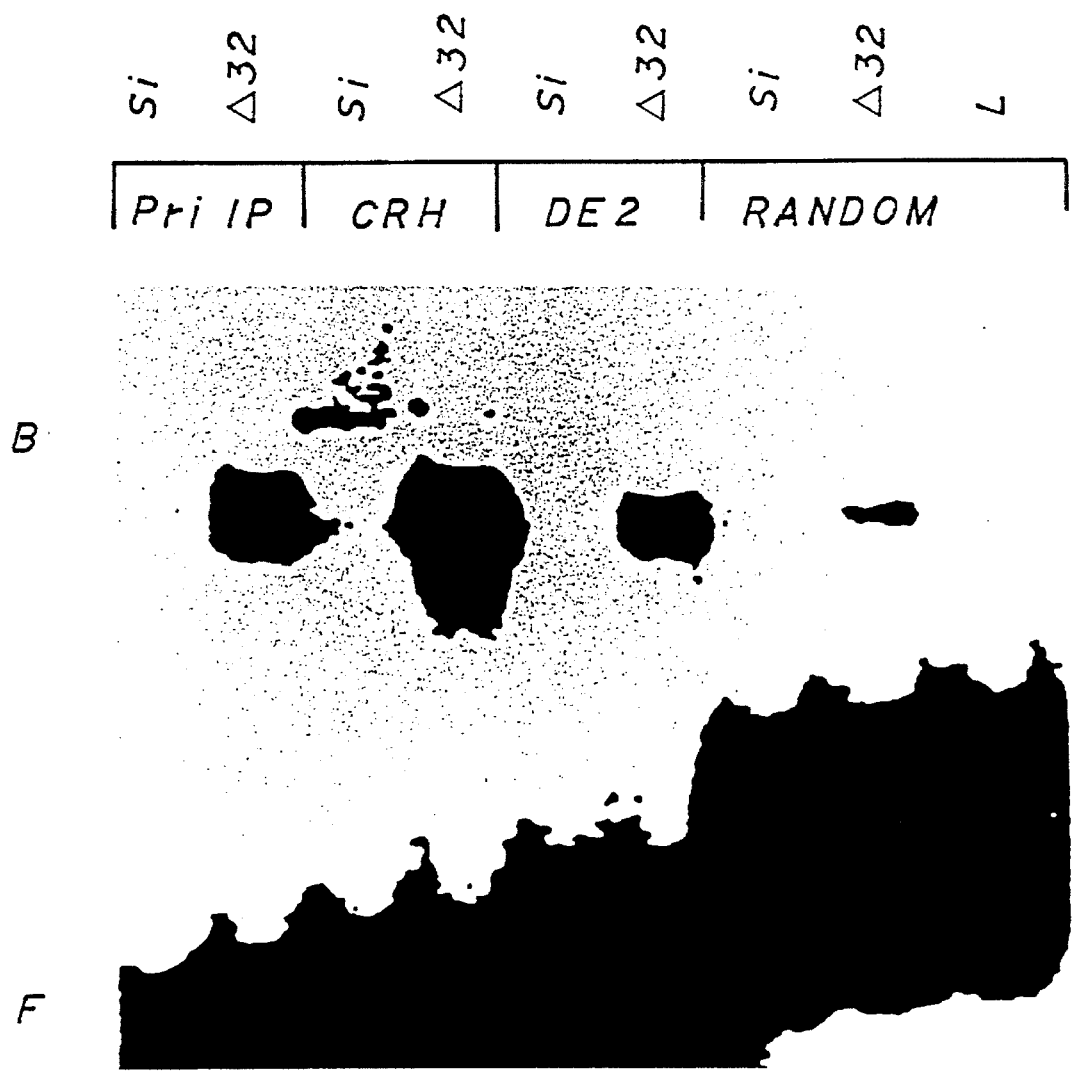
FIG. 8 depicts the results of gel-mobility shift analyses of binding at $^{32}$P-labeled sites by modified Skn-1i proteins.

Neither Skn-1i nor the ΔC version of the protein bound the Oct-Hep site. The Δ60 version, however, bound the site with an affinity comparable to Oct-2, as did the ΔN version of the protein. For comparison, as shown in FIG. 8, Skn-1i was unable to bind any of the POU domain binding sites tested whereas a truncated version of the protein from which the first 32 amino acids were deleted from the amino terminus bound all of these sites with high affinity. These data strongly suggest that as few as the first 32 amino acids from the amino terminus of Skn-1i constitute an inhibitory region which, when present, prevents the protein from binding to POU domain DNA binding sites.

C. Transferability and Function of the Skn-1i Inhibitory Region

By way of further background, although activating and partitioning regions which may be transferred to other transcription factors are known, the relatively few known inhibitory regions are not considered to be as modular in their structure and would not, therefore, be expected to be as transferable as known activating and partitioning regions (see, e.g., Sun, et al. (1991) *Cell,* 64:459; Wasylyk, et al. (1992) *Genes and Dev.* 6: 965; Ruben, et al. (1992) *Genes and Dev.* 6:745; Liou, et al. (1992) *EMBO J.* 11:3003; Baeuerle, et al. (1988) *Science* 242:540; Ghosh, et al. (1990) *Nature* 344:678; Kerr, et al. (1991) *Genes and Dev.* 5:1464; Urban, et al. (1990) *Genes and Dev.* 4:1975; Zabel, et al. (1990) *Cell* 16:255; Picard, et al. (1988) *Cell* 54:1073; and, Pratt, et al. (1988) *J. Biol. Chem.* 263:267).

Figure 10:
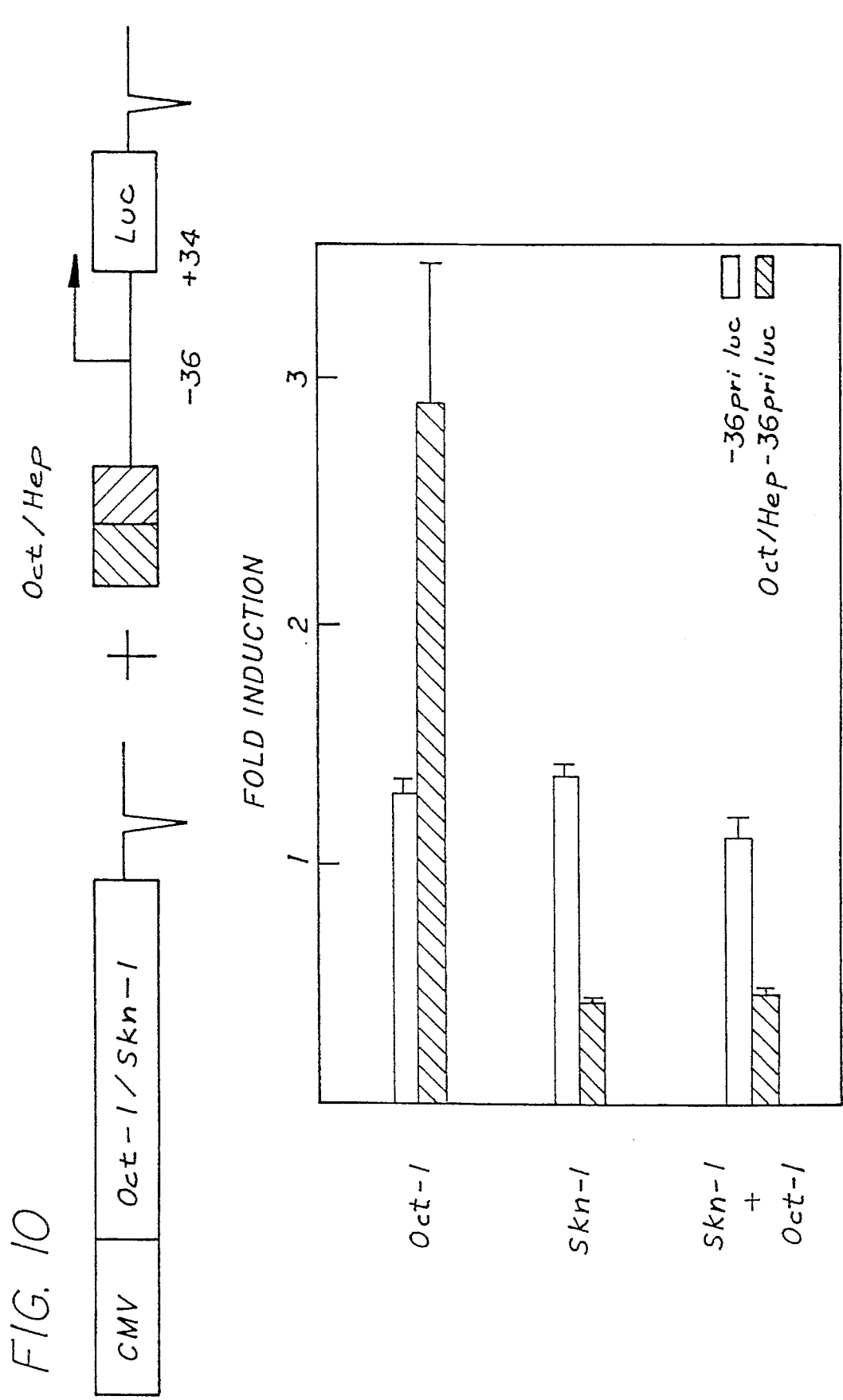
FIG. 10 depicts the results of transient transfection assays of the indicated expression plasmids into Rat-1 cells.

However, the initial 60 amino acids of the amino terminus of Skn-1i can be transferred to other, unrelated transcription factors without loss of its inhibitory effect. This is demonstrated by gel-mobility shift analyses of the binding affinity of a thyrotroph embryonic factor (TEF) (see, e.g., Drolet, et al. (1991), Genes and Dev. 5:1739), TEF/1–99 Skn-1i fusion proteins to a labeled Prl-1P site (see, FIG. 10 showing binding affinities of TEF fusions with the first 99 amino acids of Skn-1i) and Pit-1/Skn-1i fusion proteins (data not shown).

TEF/1–99 Skn-1i fusion proteins were constructed according to means well known in the art (see, Maniatis, et al., *Molecular Cloning: A Laboratory Manual* (Cold Spring Harbor Laboratory 1982)). For comparison to demonstrate the effects of removing the 60 amino acid terminus from the fusion protein, TEF/Δ60 Skn-1i fusion proteins were also constructed (using only the amino acids at positions 61–99 from Skn-1i). The fusions were performed at the amino terminus of each TEF protein used.

Figure 9:
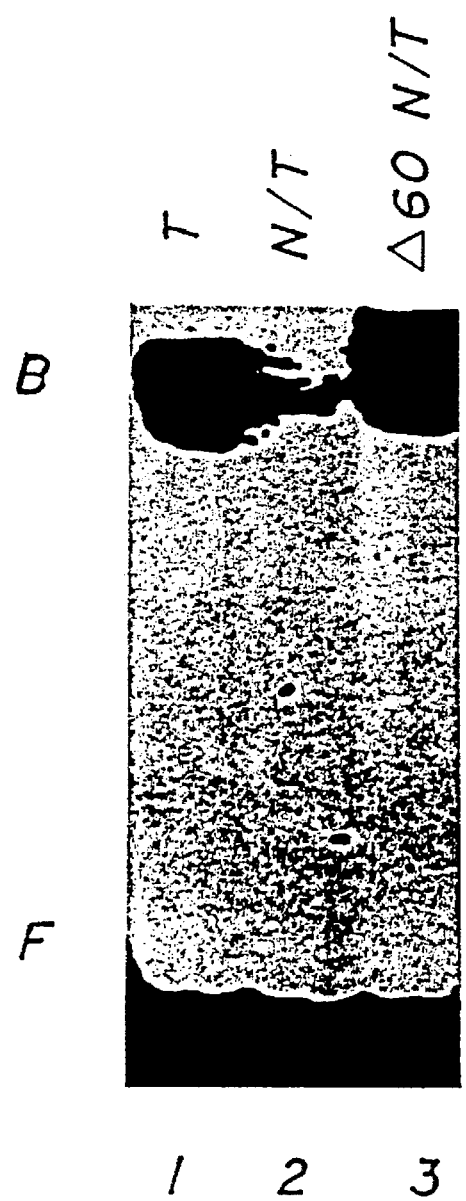
FIG. 9 depicts the results of gel-mobility shift analyses showing binding by fusion proteins having transferred portions of the Skn-1i protein therein to a labeled Pr1-1P site.

Referring to FIG. 9, along the top axis "T" identifies the band for binding of wild-type TEF, while N/T is the band for the TEF/1–99 Skn-1i construct and Δ60 N/T denotes the band for the TEF/Δ60 Skn-1i construct. Wild-type TEF proteins are known to readily bind AT-rich DNA sequences and to form homodimers and heterodimers. This binding ability was completely inhibited by the addition of 1–99 Skn-1i to the TEF amino terminus. Binding was, however, restored on removal of the first 60 amino acids (i.e., in the TEF/Δ60 Skn-1i fusion protein). These data show that (1) no alterations in TEF structure occurred during construction of the fusion proteins and (2) suggest that, although unprecedented in the art to date, the inhibitory effect of 1-60 Skn-1 i can be transferred to a transcription factor from an unrelated class.

It has been argued, and data is known in the art to suggest, that transcriptional factors which serve to activate transcription can, in any combination, work synergistically by direct interaction with each other (see, e.g., Ptashne (1988) *Nature* 335:683–689). The transferability of activating and partitioning regions in other transcription factors, conservation of inhibitory function in the TEF/1–99 Skn-1i fusion protein, the fact TEF's status as a member of the B-Zip gene family not related to POU domain transcription factors, and the fact that many members of the POU domain and other gene families, though otherwise structurally diverse, are known to contain regions rich in specific amino acids (e.g., serine/threonine, glutamine and glycine/alanine), all suggest that the DNA binding abilities of many transcription factors within and without the POU domain gene family may be inhibited by fusion with, or other direct influence by, 1–60 Skn-1i.

For example, the fact that (as demonstrated above) Skn-1i transcripts are most abundant in post-mitotic cells of the superficial layer of the epidermis logically suggests that it could inhibit the actions of Oct-1 that are thought to be important in cellular proliferation events (for example, stimulation of DNA replication and transcription in adenoviruses, transcription of a human histone H2b gene and activation of the U2 promoter).

This supposition was confirmed in transient transfection assays performed as follows: Oct/Hep-36 prl luc (a reporter plasmid containing a reporter/luciferase gene under the control of a minimal promoter and the immunoglobulin octamer/heptamer element described elsewhere above) as well as expression plasmids containing the Skn-1i and Oct-1 transcription units were constructed. The expression plasmids (0.5 µg) and the reporter plasmids (3.0 µg) were transfected into Rat-1 fibroblasts and HeLa cells. After cells were plated at low density the day prior to transfection, as a control, the expression plasmids were also transfected into Rat-1 fibroblasts which contained the reporter plasmids without the octamer/heptamer element therein.

Transfection was performed by the calcium phosphate method described in Drolet, et al. (1991), *Genes and Dev.* 5:1739. Cells were harvested after 48 hours and luciferase activity measured by assay, according to means well-known in the art, the results of which are depicted in FIG. 10(*a*). Referring to FIG. 10, the side axis refers to the effect on reporter gene expression by 0 (Oct-1), Si (Skn-1i) and, by co-transfection a Skn-1i containing plasmid and an Oct-1 containing plasmid. The dark bars reflect Oct/hep-36 prl luc expression; the light bars show, as a baseline, the expression of −36 prl luc (i.e., a luciferase/promoter plasmid).

These data demonstrate that Skn-1i inhibited the stimulatory effects of Oct-1 on octamer/heptamer gene expression. This effect is apparently specific because, using similar experimental protocol to demonstrate the effect of Skn-1i on the minimal promoter itself (see FIG. 11), as well as cAMP and estrogen response elements Skn-1i failed to inhibit and decrease their levels of expression from normally expected levels. Taken together, therefore, these data suggest that Skn-1i inhibits Oct-1 effects on gene expression in epidermis.

Figure 11:
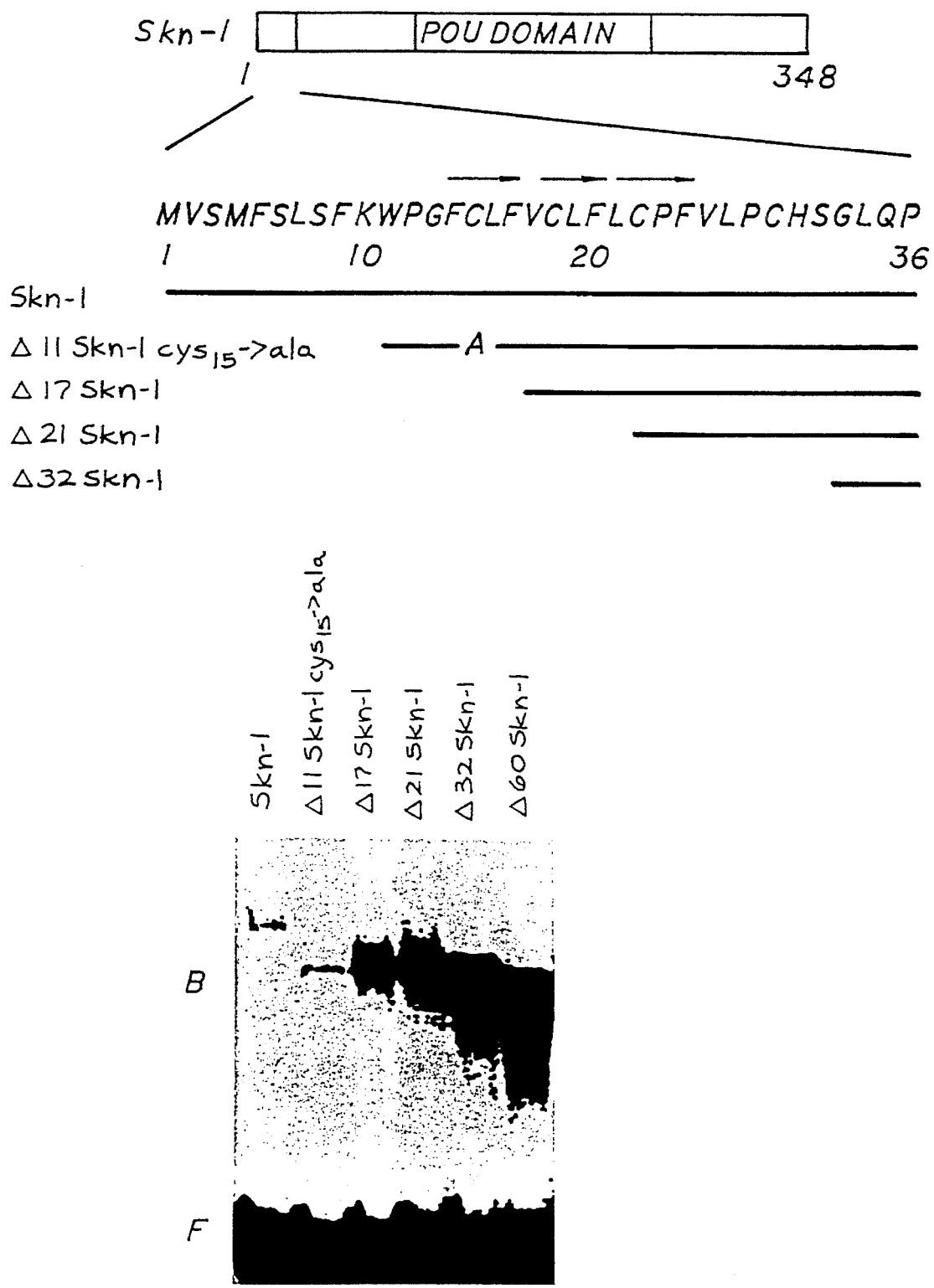
FIG. 11 depicts the results of solution crosslinking assays of the indicated $^{35}$S-labeled proteins.

Although the inhibitory effect of Skn-1i is obtained with the presence of the first 60 amino acids of the protein, inhibition is also completely obtained with a 21 amino acid region extending from position 11 to 32. Incomplete inhibition was also obtained with amino acids 17 to 32 and 21 to 32, respectively. Truncated versions of Skn-1i constructed as described with respect to FIG. 8 above (referred to respectively as Δ11, Δ17, Δ21, Δ32 and Δ60) were tested for octamer binding in a gel-mobility shift assay as described with respect to FIG. 9. The results of the assay of these truncated versions are depicted in FIG. 11, demonstrating that the greatest binding occurs with deletion of amino acids 32–60 (which, therefore, exert the greatest inhibitory effect on binding when present as shown in the Si and Δ11 bands).

How the inhibitory region of Skn-1i asserts its effect is less clear. However, from the following data it can be predicted that it (1) is selective for protein-DNA interaction rather than homodimer formation, and (2) does not require zinc coordination for function.

With respect to (1), the effect of the Skn-1i inhibitory region on dimerization in solution was assayed by the ability of a homobifunctional crosslinking agent [disuccnidyl suberate (DSS)] to crosslink in vitro translated proteins.

Specifically, approximately 100,000 cpm of $^{35}$S-labeled Skn-1i, Δ32Skn-1i, 1–99 (N/T) Skn1-i and Δ60 (N/T) Skn1-i proteins were added separately to 20 ml of binding buffer (10 mM HEPES [pH7.8], 50 mM K CI, 5% glycerol). After 15 minutes at room temperature, 0.5 mil of DSS (suspended in 5 mg/ml DMSO) or DMSO alone was added to each of the reactions. After 5 minutes, the reaction was stopped by adding SDS sample buffer to each which was then boiled prior to analyses on SDS/polyacrylamide gels. To quantitate crosslinking efficiency, monomers ("M" on FIG. 12) and dimers ("D" on FIG. 12) were excised from the gel and counted by scintillation counting.

Figure 12:
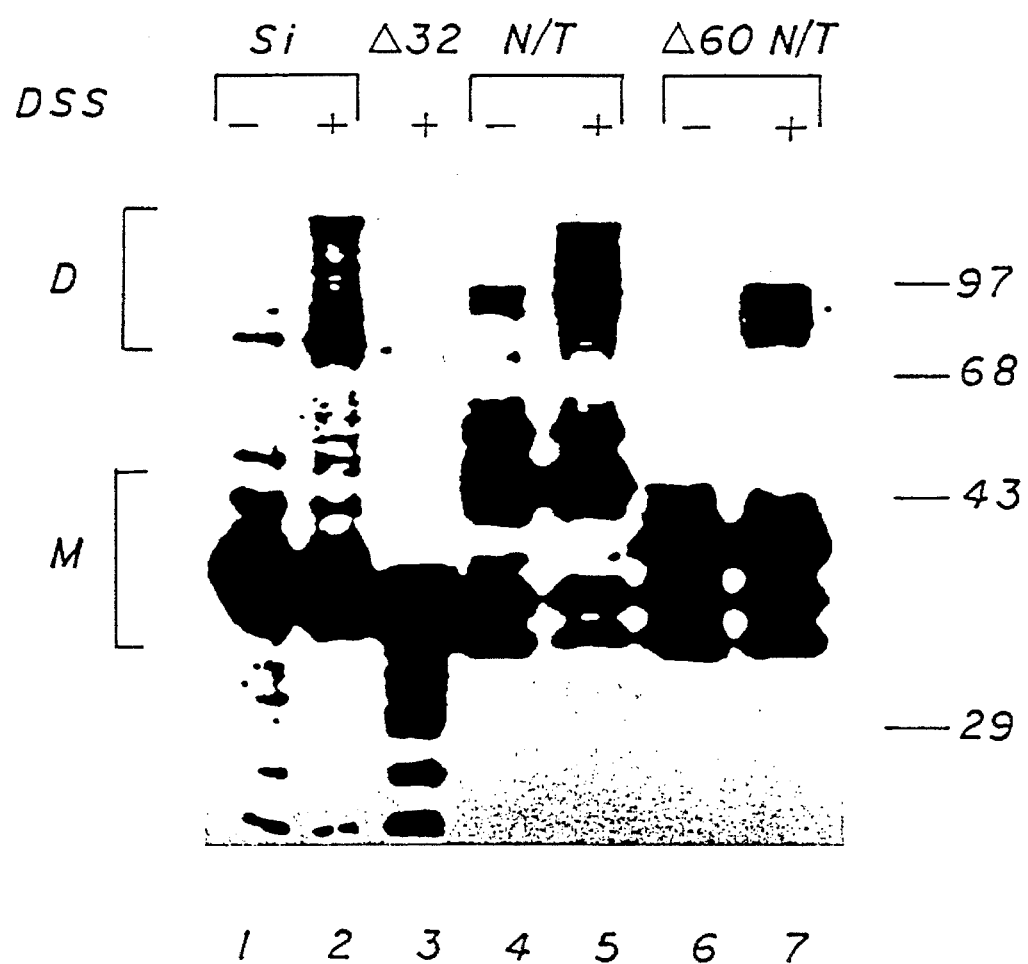
FIG. 12 depicts the results of gel-mobility shift analyses showing binding by the Skn-1i protein and mutations thereof to a $^{32}$P-labeled octamer-heptamer element.

Referring to FIG. 12, comparison of the N/T and Δ60 N/T bands reveals that the amount of dimer formed with each was similar (approximately 13%). (Minor bands most likely represent products initiated from internal methionines). The full Skn-1i protein also exhibited crosslinking in solution while no crosslinking was not evident with Δ32 Skn-1i. These data indicate that the inhibitory domain may provide a protein-protein interaction interface.

Figure 13:
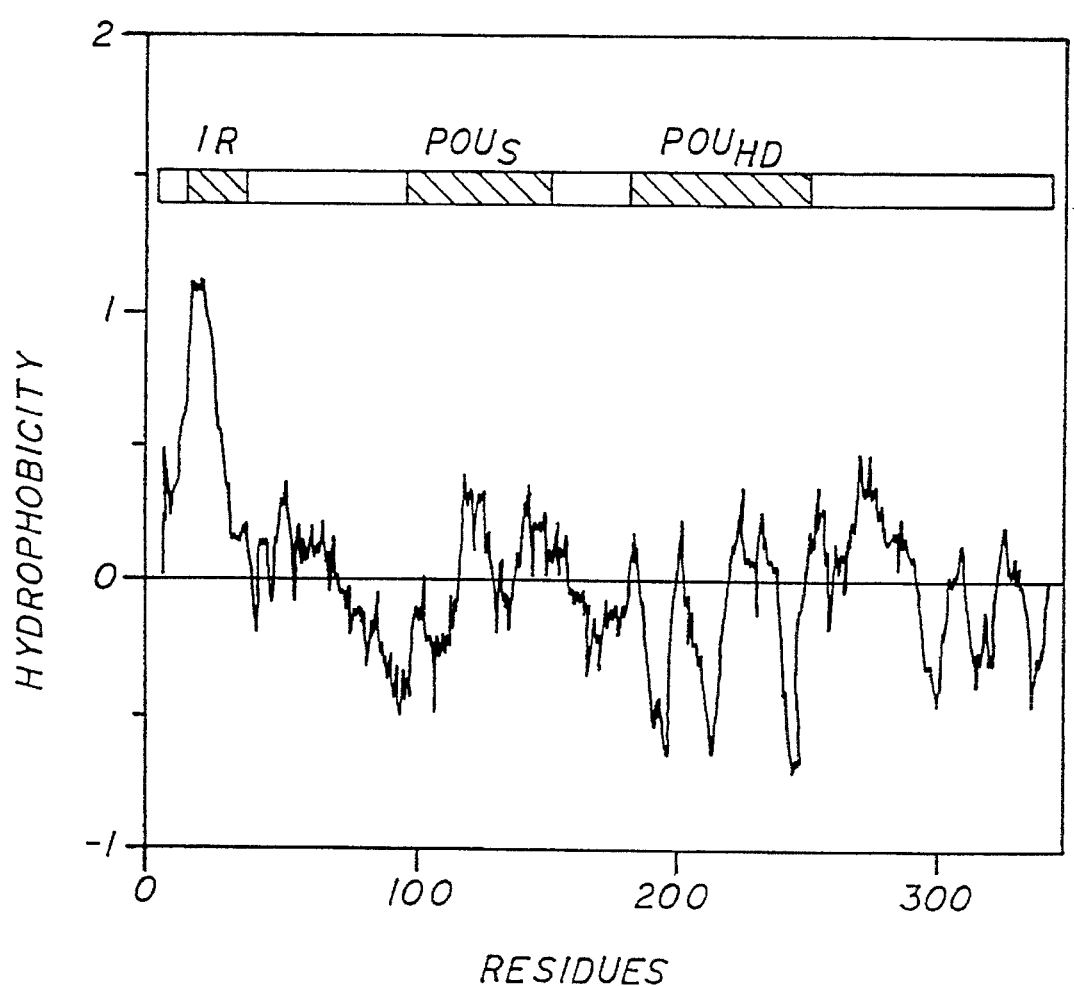
FIG. 13 depicts a normalized Kite-Doolittle hydropathy profile of the Skn-1a/i proteins.

Finally, with regard to (2), reference to FIG. 13 shows a normalized hydropathy profile for Skn-1i derived from the Kyte-Doolittle algorithm described in Kyte, et al. (1982) *J. Mol. Biol.* 157:105. This profile reveals the inhibitory region to be highly hydrophobic. Further, although this region contains a four amino acid motif repeated thrice and four cysteines separated by 3,3 and 5 amino acids with a subsequent histidine residue (consistent with a potential zinc finger structure; see FIG. 2), mutation of cysteine residue 15 (FIG. 9) did not allow DNA binding.

In addition, although EDTA would normally bind zinc, it did not block the inhibitory effects of Skn-1; when the protein was added at approximately 25,000 cpm to 10 mM EDTA, thus indicating that zinc coordination is unlikely to be crucial for this domain.

In summary, the inhibitory region of POU domain protein Skn-1i is at least an 11 and up to 60 amino acid region which is transferable to other transcription factors, apparently including those outside of its class. The inhibitory region is outside of the POU DNA binding domain, does not require zinc coordination for function and apparently provides an interface for protein-protein interactions. The gene for the protein is present and expressed in epidermal and hair follicle cells, with expression occurring in a tissue and stage-specific manner through development of the embryo and growth of adult tissues.

D. Existence and Function of Alternative Form Skn-1a

Following the same screening and isolation methods described above with respect to Skn-1i, a second RNA transcript was identified and, ultimately, isolated. Specifically, RNA from rat neonatal skin was used with random hexamers and reverse transcriptase (from AMV; available from Promega of Madison, Wis.) to generate cDNA's which were cloned into a λ ZAP II vector obtained commercially from Stratagene of La Jolla, Calif. This library was screened with a $^{32}$P-labeled probe corresponding to the entire amino terminus and the POU domain of Skn-1i.

Three independent clones were identified and isolated which together corresponded to the entire common region between Skn-1i and Skn-1a (from nucleotide 383 to 612; see, SEQ ID No:3). The SEQ ID No: 3 sequence was obtained by the dideoxy nucleotide replication method described with respect to identification of SEQ ID No:1 above. The Skn-1a clone contains, as a result of alternative splicing, a sequence predicting a 113 amino acid sequence from its amino terminus as shown in SEQ ID No:4, which replaces the first 31 residues of Skn-1i (shown in SEQ ID No:2). Using the same PCR and RNase protection assay methods as described with respect to Skn-1i, expression in skin was also demonstrated for the Skn-1a gene; although its relative ratio of expression with respect to Skn-1i has not as yet been determined. It is expected, however, that these ratios may be readily determined in the same manner described above for determination of the pattern of expression for Skn-1i.

Figure 14:
FIG. 14 depicts the results of an RNase protection assay demonstrating expression of the Skn-1a gene in skin cells.

To confirm expression of Skn-1a in adult rat and mice skin cells, a RNase protection assay was performed as described with respect to expression of Skn-1i in epidermis, skeletal muscle, tongue, esophagus, heart, thymus, spleen, liver, kidney, testis, adrenals, placenta, lungs, brain and anterior pituitary above (see, *Current Protocols in Molecular Biology*, supra at Unit 4.7). The results of this assay are depicted in FIG. 14.

Figure 15:
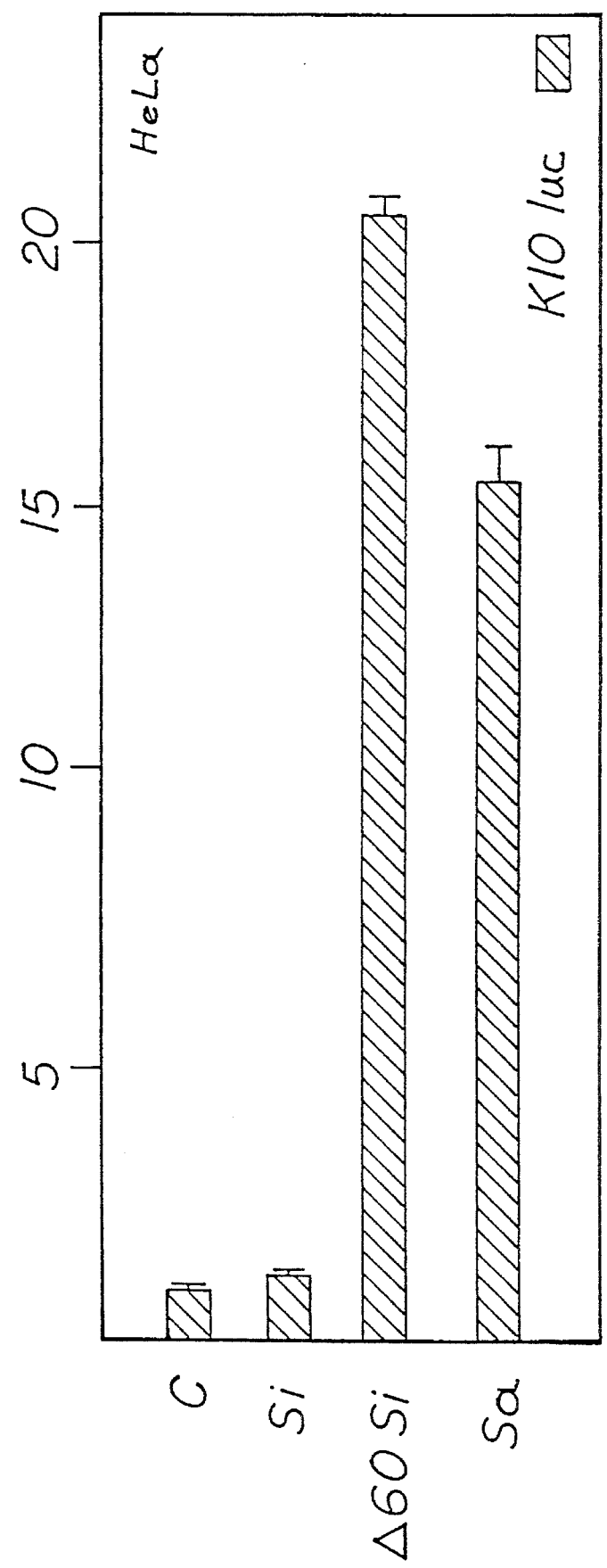
FIG. 15 depicts the results of transient transfection assays of the indicated expression plasmids in HeLa cells.

Referring to FIG. 15, to determine the function of Skn-1a, a co-transfection assay modeled after the one described with respect to FIG. 10 was performed. Plasmids were constructed according to well-known means (see, e.g., Drolet, et al., (1991) Genes and Dev., 5:1739, et seq.) with the luciferase ("IUC") reporter gene and a cytokeratin 10 (K10) promoter, the latter of which contains 1665 bp of 5' flanking and untranslated sequence from the K10 gene which is known to be a marker for terminally differentiating epidermal keratinocytes. Included in separate plasmids were, respectively, K10-luc; Skn-1i ("Si" in FIG. 16); Δ60 Skn-1i ("Δ60Si" in FIG. 15); and Skn-1a ("Sa" in FIG. 15). 0.5 μg of each expression plasmid and 3.0 μg of the reporter plasmid were transfected in HeLa cells, with the reporter gene alone being separately transfected as a control ("C" in FIG. 15). Cells were harvested after 48 hours and luciferase activity measured.

As shown by the data depicted in FIG. 15, although Skn-1i had minimal effect on the K10 promoter, Skn-1a was a potent activator of it. However, because Δ60 Skn-1i also strongly activated the promoter, it can be predicted that the critical function of Skn-1a on the K10 promoter is to relieve the action of the Skn-1i inhibitory region (where present) rather than serving as a direct transactivation domain.

Referring to FIG. 16, another co-transfection assay was performed which demonstrated that Skn-1a strongly activates a promoter of a human papilloma virus (HPV-1).

To perform the assay, luciferase plasmids were constructed according to the techniques described with respect to FIG. 16. HPV-1 was obtained from the American Type Culture Collection (accession No. 45021; a pHPV-1 plasmid constructed by inserting the entire viral genomic DNA linearized at Bam H1 site into Bam H1 site of pBR322). Generally, the HPV-1 plasmid used for the assay of FIG. 16 was constructed by including the LCR (long control region) regulatory region of HPV-1 before the luciferase gene. Separate plasmids including Skn-1a were co-transfected into HeLa cells with the HPV-1LCR-luc plasmids; the latter plasmids were separately transfected alone to establish a baseline level of expression.

As shown in FIG. 16, luciferase activity indicating expression of viral proteins in cells by the HPV-1 gene increased 7.46 fold in the presence of Skn-1a, thus indicating that Skn-1a is a potent activator of the HPV-1LCR promoter. Interestingly, the addition of plasmids (under the control of the well-known CMV promoter) including the HPV-1 gene coding regions for the E6 viral proteins to cells having both the Skn-1a plasmid and the HPV-1 LCR-luc plasmids showed, respectively, a 92.38 fold increase in luciferase activity while a 107.73 fold increase was exhibited in the presence of plasmids encoding for the E7 viral protein.

One probable explanation for the substantial enhancement of expression in the presence of the viral proteins is that they work in synergy with Skn-1a to trigger a feed forward mechanism. More particularly, it is probable that Skn-1a serves to activate the HPV-1 promoter, resulting in the expression of gene products (including E6 and E7), which in turn further stimulate the promoter to cause expression of viral gene products at greater levels.

Because of the presence of highly conserved regions among papillomavirinae (see, e.g., Fields, et al., *Virology* (Raven Press, Ltd., 2d ed. 1990), Ch. 58), it can be predicted that Skn-1a would activate expression of gene products by many if not all members of the papilloma virus family. It may even be (at least in the case of HPV-1) that Skn-1a is required to stimulate gene expression by papilloma viruses. Given the widespread potential distribution of papillomavirinae in derreal tissues, this insight into the probable etiological role of Skn-1a may prove to be important in the control or treatment of disease caused by or related to these viruses.

E. Expression of Skn-1i in Human Keratinocytes

As noted above, it can be predicted, based on sequence homologies with rat and mouse Skn-1i/a and known characteristics of mammalian transcription factors that the gene will be similarly expressed, resulting in proteins having similar function, in human skin. This prediction is borne out by the following data.

Figure 17:
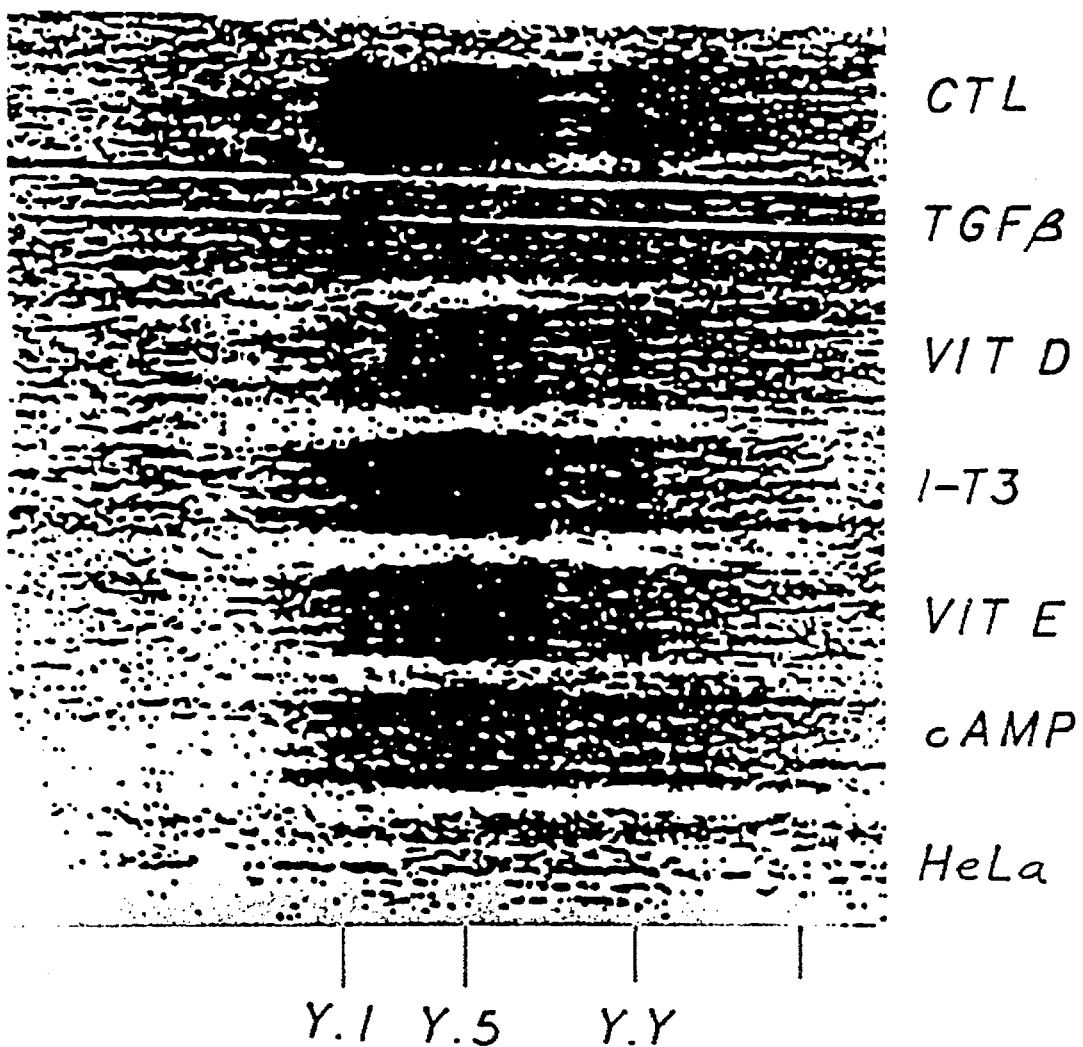
FIG. 17 depicts the results of a Northern blot using Skn-1i/a cDNA as a probe to show the presence of Skn-1i/a RNA in human keratinocytes.

Referring to FIG. 17, results of Northern blot analyses are depicted showing the presence of Skn-1i/a protein in human keratinocytes. These analyses were performed substantially as described in *Current Protocols in Molecular Biology*, supra at Unit 4.9 using Skn-1i/a as the probe. Human foreskin keratinocytes were used to extract polyadenylated RNA, which was size fragmented by denaturing gel electrophoresis according to means well-known in the art, and transferred to nitrocellulose. Hybridization with a Skn-1i/a specific cDNA probe (described supra) revealed the presence of a specific Skn-1i/a reactive transcript.

FIG. 17, along the top axis, depicts comparison blots using cells with no added hormone ("CTL", for control), TGFβ, Vitamin D, thyroid hormone (I-T3), Vitamin E and cAMP. The panel showing hybridization with the Skn-1i/a probe is at the leftmost panel.

It will be understood by those skilled in the art that modifications to and expansions of the above data and predictions therefrom may be made without departing from the spirit and scope of the invention, which is defined solely by the appended claims.

SUMMARY OF SEQUENCES

SEQUENCE ID No:1 is the nucleic acid (and deduced amino acid) sequence for the full-length Skn-1i clone, including untranslated and translated regions.

SEQUENCE ID No:2 is the deduced amino acid sequence for the Skn-1i clone.

SEQUENCE ID No:3 is the nucleic acid (and deduced amino acid) sequence for the full-length Skn-1a clone, including untranslated and translated regions.

SEQUENCE ID No:4 is the deduced amino acid sequence for the full-length Skn-1a clone.

We claim:

1. A DNA molecule having a nucleotide sequence which consists of the nucleotide sequence of SEQ ID No:1.

2. An expression vector containing a DNA sequence having the nucleotide sequence of SEQ ID No: 1.

3. An isolated and substantially pure DNA molecule having a nucleotide sequence encoding a polypeptide possessing at least one biological activity, said biological activity comprising inhibition of binding of DNA having the octamer site 5'-ATGCAAAT-3' therein by mammalian transcription factors which can bind to said octamer site, wherein said encoded polypeptide has the amino acid sequence of SEQ ID No. 2.

4. A DNA molecule according to claim 3 wherein said biological activity is exerted by a region of said sequence encoding at least the first 60 amino acids at the amino terminus of said encoded polypeptide.

5. A DNA molecule according to claim 3 wherein said biological activity is exerted by a region of said sequence encoding at least the first 32 amino acids at the amino terminus of said encoded polypeptide.

6. A DNA molecule according to claim 3 wherein said biological activity is exerted by a region of said sequence encoding 21 amino acids from amino acids 11 through 32 in SEQ.ID.No.2.

7. A DNA molecule according to claim 3 wherein said encoded polypepe tide inhibits DNA binding by transcription factors encoded by members of the POU domain gene family.

8. A DNA molecule according to claim 7 wherein at least one of said transcription factors inhibited by said encoded polypeptide is Oct-1.

9. A DNA molecule according to claim 3 wherein said encoded polypeptide inhibits DNA binding by transcription factors encoded by members of the B-Zip gene family.

10. A DNA molecule according to claim 9 wherein at least one of said transcription factors inhibited by said encoded polypeptide is thyrotroph embryonic factor.

11. An isolated and substantially pure RNA molecule having a nucleotide sequence encoding a polypeptide possessing at least one biological activity, said biological activity comprising inhibition of binding of DNA having the octamer site 5'-ATGCAAAT-3' therein by mammalian transcription factors which can bind to said octamer site, wherein said polypeptide has the amino acid sequence of SEQ ID No. 2.

12. A RNA molecule to claim 11 wherein the molecule is 2.3 kb in size.

13. A RNA molecule according to claim 11 wherein said mammalian transcription factors are those found in mammalian skin.

14. A RNA molecule according to claim 11 wherein said biological activity is exerted by a region of said sequence encoding at least the first 60 amino acids at the amino terminus of said encoded polypeptide.

15. A RNA molecule according to claim 11 wherein said biological activity is exerted by a region of said sequence encoding at least the first 32 amino acids at the amino terminus of said encoded polypeptide.

16. A RNA molecule according to claim 11 wherein said biological activity is exerted by a region of said sequence encoding 21 amino acids from amino acids 11 through 32 in SEQ. ID. No. 2.

17. A RNA molecule according to claim 11 wherein said encoded polypeptide inhibits DNA binding by transcription factors encoded by members of the POU domain gene family.

18. A RNA molecule according to claim 17 wherein at least one of said transcription factors inhibited by said encoded polypeptide is Oct-1.

19. A RNA molecule according to claim 11 wherein said encoded polypeptide inhibits DNA binding by transcription factors encoded by members of the B-Zip gene family.

20. A RNA molecule according to claim 19 wherein at least one of said transcription factors inhibited by said encoded polypeptide is thyrotroph embryonic factor.

21. An expression vector containing a DNA sequence which encodes a polypeptide possessing at least one biological activity, said biological activity comprising binding of DNA having the octamer site 5'-ATGCAAAT-3' therein by mammalian transcription factors which bind to said octamer site, wherein said polypeptide has the amino acid sequence of SEQ ID No: 2.

22. A DNA molecule having a nucleotide sequence which consists of the nucleotide sequence shown in SEQ ID No:3.

23. An expression vector containing a DNA sequence having the nucleotide sequence of SEQ. ID. No. 3.

24. An isolated and substantially pure DNA molecule having a nucleotide sequence encoding a polypeptide possessing at least one biological activity, said biological activity consisting of activation of expression by DNA having the octamer site 5'-ATGCAAAT-3' therein by mammalian transcription factors which can bind to said octamer site, wherein said polypeptide has the amino acid sequence of SEQ ID No: 4.

25. A DNA molecule according to claim 24 wherein said mammalian transcription factors are those found in mammalian skin.

26. An isolated and substantially pure RNA molecule having a nucleotide sequence encoding a polypeptide possessing at least one biological activity, said biological activity consisting of activation of expression by DNA having the octamer site 5'-ATGCAAAT-3', wherein said polypeptide has the amino acid sequence of SEQ ID No: 4.

27. A RNA molecule according to claim 26 wherein said biological activity is activation of expression by DNA in mammalian skin.

28. An expression vector containing a DNA sequence which encodes a polypeptide possessing at least one biological activity, said biological activity comprising binding of DNA having the octamer site 5'-ATGCAAAT-3' therein by mammalian transcription factors which bind to said octamer site, wherein said polypeptide has the amino acid sequence of SEQ ID No: 4.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 2192 base pairs
      ( B ) TYPE: nucleic acid
      ( C ) STRANDEDNESS: single
      ( D ) TOPOLOGY: linear ( i i ) MOLECULE TYPE: cDNA ( v i i ) IMMEDIATE SOURCE:
      ( B ) CLONE: Skn-1i ( i x ) FEATURE:
      ( A ) NAME/KEY: CDS
      ( B ) LOCATION: 279..1325

( x i ) SEQUENCE DESCRIPTION: SEQ ID NO:1:

| | | | | | |
|---|---|---|---|---|---|
| CGCTGTAGTC | ATTCCTGTGT | CCTCTTCTCT | CTGGGCTTCT | CACCCTGCTA | ATCAGATCTC | 60 |
| AGGGAGAGTG | TCTTGACCCT | CCTCTGCCTT | TGCAGCTTCA | CAGGCAGGCA | GGCAGGCAGG | 120 |
| CAGGACAGGT | TTGGGGACTC | TGTTTACAGC | TGTTTATCCC | AGAGTCTGGT | CGGCCTCCAC | 180 |
| CTGATGTGGC | AATTGCTGGC | AGTGCCACAG | GCTTTTCAGC | CAGGCTTAGG | GTGGGTTCTG | 240 |

```
GGACCTGATT AGGTGAGCAG GAGGAGGGGG CAGTTAGC ATG GTT TCA ATG TTC                293
                                           Met Val Ser Met Phe
                                            1               5

AGC TTG TCT TTC AAA TGG CCT GGA TTT TGT TTG TTT GTT TGT TTG TTC              341
Ser Leu Ser Phe Lys Trp Pro Gly Phe Cys Leu Phe Val Cys Leu Phe
             10                  15                  20

CTT TGT CCC TTT GTC CTC CCC TGT CAC TCA GGT CTG CAG CCG AAT CTT              389
Leu Cys Pro Phe Val Leu Pro Cys His Ser Gly Leu Gln Pro Asn Leu
             25                  30                  35

CTC TCC TTT CCA CAG CAA CAG AGC ACT CTA CTC CTC CCA CAG ACA GGA              437
Leu Ser Phe Pro Gln Gln Gln Ser Thr Leu Leu Leu Pro Gln Thr Gly
             40                  45                  50

CCT GGC CTC ACC TCC CAG GCA GTT GGA CGC CCT GGG CTG TCA GGA TCC              485
Pro Gly Leu Thr Ser Gln Ala Val Gly Arg Pro Gly Leu Ser Gly Ser
 55                  60                  65

TCT TTA GAG CCC CAC CTG GAA GCT TCT CAA CAT CTG CCA GGG CCC AAG              533
Ser Leu Glu Pro His Leu Glu Ala Ser Gln His Leu Pro Gly Pro Lys
 70                  75                  80                  85

CAT CTG CCT GGC CCC GGA GGG AAT GAC GAA CCC ACT GAC CTG GAG GAG              581
His Leu Pro Gly Pro Gly Gly Asn Asp Glu Pro Thr Asp Leu Glu Glu
                 90                  95                 100

CTG GAG AAG TTC GCC AAG ACC TTC AAG CAG AGG CGC ATA AAG CTA GGC              629
Leu Glu Lys Phe Ala Lys Thr Phe Lys Gln Arg Arg Ile Lys Leu Gly
            105                 110                 115

TTC ACA CAG GGG GAT GTG GGA TTG GCG ATG GGA AAG CTG TAT GGT AAC              677
Phe Thr Gln Gly Asp Val Gly Leu Ala Met Gly Lys Leu Tyr Gly Asn
            120                 125                 130

GAC TTC AGC CAG ACT ACC ATC TCG AGA TTT GAG GCC CTC AAC CTG AGT              725
Asp Phe Ser Gln Thr Thr Ile Ser Arg Phe Glu Ala Leu Asn Leu Ser
            135                 140                 145

TTC AAG AAC ATG TGT AAA CTC AAG CCA CTG CTG GAG AAG TGG CTG AAT              773
Phe Lys Asn Met Cys Lys Leu Lys Pro Leu Leu Glu Lys Trp Leu Asn
150                 155                 160                 165

GAT GCA GAG TCC TCC CCG GCA GAC CCT TCA GCA AGC ACT CCC AGC TCG              821
Asp Ala Glu Ser Ser Pro Ala Asp Pro Ser Ala Ser Thr Pro Ser Ser
                170                 175                 180

TAC CCC ACT CTC AGC GAA GTA TTT GGC AGG AAG AGG AAG AAA CGG ACC              869
Tyr Pro Thr Leu Ser Glu Val Phe Gly Arg Lys Arg Lys Lys Arg Thr
                185                 190                 195

AGC ATC GAG ACC AAC ATC CGC CTG ACT TTG GAG AAG CGA TTT CAA GAT              917
Ser Ile Glu Thr Asn Ile Arg Leu Thr Leu Glu Lys Arg Phe Gln Asp
                200                 205                 210

AAC CCT AAA CCC AGC TCG GAA GAG ATT TCC ATG ATT GCG GAG CAG TTG              965
Asn Pro Lys Pro Ser Ser Glu Glu Ile Ser Met Ile Ala Glu Gln Leu
215                 220                 225

TCC ATG GAG AAG GAA GTG GTA AGA GTC TGG TTC TGC AAT CGA CGC CAA             1013
Ser Met Glu Lys Glu Val Val Arg Val Trp Phe Cys Asn Arg Arg Gln
230                 235                 240                 245

AAG GAG AAG AGA ATC AAC TGC CCT GTG GCC ACA CCT GTC AAG CCG CCC             1061
Lys Glu Lys Arg Ile Asn Cys Pro Val Ala Thr Pro Val Lys Pro Pro
                250                 255                 260
```

| | | | | | | | | | | | | | | | | |
|---|---|---|---|---|---|---|---|---|---|---|---|---|---|---|---|---|
| ATC | TAC | AAC | TCC | CGG | CTG | GTC | TCT | CCC | TCA | GGG | TCT | CTG | GGC | TCC | CTC | 1109 |
| Ile | Tyr | Asn | Ser | Arg | Leu | Val | Ser | Pro | Ser | Gly | Ser | Leu | Gly | Ser | Leu | |
| | | | 265 | | | | | 270 | | | | | 275 | | | |
| TCA | GTC | CCT | CCT | GTC | CAC | AGC | ACC | ATG | CCT | GGA | ACA | GTA | ACG | TCA | TCC | 1157 |
| Ser | Val | Pro | Pro | Val | His | Ser | Thr | Met | Pro | Gly | Thr | Val | Thr | Ser | Ser | |
| | | 280 | | | | | 285 | | | | | 290 | | | | |
| TGT | TCC | CCT | GGG | AAC | AAC | AGC | AGG | CCC | TCG | TCT | CCC | GGC | TCA | GGA | CTC | 1205 |
| Cys | Ser | Pro | Gly | Asn | Asn | Ser | Arg | Pro | Ser | Ser | Pro | Gly | Ser | Gly | Leu | |
| | 295 | | | | | 300 | | | | | 305 | | | | | |
| CAT | GCC | AGC | AGC | CCC | ACG | GCA | TCT | CAA | AAT | AAC | TCC | AAA | GCA | GCA | ATG | 1253 |
| His | Ala | Ser | Ser | Pro | Thr | Ala | Ser | Gln | Asn | Asn | Ser | Lys | Ala | Ala | Met | |
| 310 | | | | | 315 | | | | | 320 | | | | | 325 | |
| AAC | CCC | TCC | TCC | GCC | GCC | TTT | AAC | TCC | TCA | GGG | TCA | TGG | TAC | CGT | TGG | 1301 |
| Asn | Pro | Ser | Ser | Ala | Ala | Phe | Asn | Ser | Ser | Gly | Ser | Trp | Tyr | Arg | Trp | |
| | | | | 330 | | | | | 335 | | | | | 340 | | |
| AAC | CAT | CCC | GCC | TAC | CTC | CAC | TGAGACCAAA | | AACTTCCTCC | | CGTTCCACCT | | | | | 1352 |
| Asn | His | Pro | Ala | Tyr | Leu | His | | | | | | | | | | |
| | | | 345 | | | | | | | | | | | | | |

| | | | | | |
|---|---|---|---|---|---|
| GGCCCTGGTT | CCCACCAGGA | GGAAGAGCGG | CCACACCTTC | CACGTATGGA | CAGACACTTT | 1412 |
| GAGACTCGGA | GCGGGAGAAA | TGGCCGCTGC | TGAAGAGCAA | ACCCACAATC | TTGCCTTCTC | 1472 |
| CTGGATCCAG | AGCTTCCAGA | GAACCAAGAT | GTGACCAAAG | GCGCACACTC | TTGCCTTGGG | 1532 |
| CTCTTGATCA | CCCGCTGGGA | GTTTACCGTG | CTCACCCGTG | ACCGCTTCAT | GCTCACATGA | 1592 |
| TGGCTCACCT | ATTGGAAAGG | CATTCTGCCA | TTGTTAGTTT | TCAGCTCACC | GGTGGGATTC | 1652 |
| TGGGACAGCC | TTTTGCTCGT | TGTGCCAAAC | TGCAAGAAGG | GTAGTTATGG | TTTTGACTCT | 1712 |
| GACCTCAGCC | ACAATCCTGA | ACTGATCCAA | ATTCTATGAG | AAGACTGAAA | TCTCGTGTCT | 1772 |
| CTACCAAAGC | TTATTTTGT | TAAATTAGCA | CAGTTTTCTT | ACAGCATATC | CATTTTGCC | 1832 |
| CAACTTTCTT | TTAGAAATTA | CTTCCCTTTT | CTACAACAAA | ACCTGTCTAT | CCTTAGGTCC | 1892 |
| TACAAAGTCC | CTTCCTCTCT | ATAAATGGCT | AAGCTCCCCT | CTGGCCATGT | TGCTCCATTC | 1952 |
| ACGTGTACTC | TTTTGTTGCC | CACATGTTCC | CAAGTTCAAG | AACACTTGTT | TTTTTCTGT | 2012 |
| TCTCTGTGGG | TTTTCTTGTC | CTGTCCCCTC | TCCTTGCTCC | TGGCCACAGA | GAAGTACACA | 2072 |
| CACTGTGGCC | ACTTTCTTGT | ACATAGTCCT | TTCCTACTCT | GCACTATGAC | CGTTCATCTT | 2132 |
| TAATGTGTAA | TTTCCCAGCG | AAATGTTTAA | CTCAGGTGTG | CATTTGAAA | AAAAAAAAA | 2192 |

(2) INFORMATION FOR SEQ ID NO:2:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Val | Ser | Met | Phe | Ser | Leu | Ser | Phe | Lys | Trp | Pro | Gly | Phe | Cys | Leu |
| 1 | | | | 5 | | | | | 10 | | | | | 15 | |
| Phe | Val | Cys | Leu | Phe | Leu | Cys | Pro | Phe | Val | Leu | Pro | Cys | His | Ser | Gly |
| | | | 20 | | | | | 25 | | | | | 30 | | |
| Leu | Gln | Pro | Asn | Leu | Leu | Ser | Phe | Pro | Gln | Gln | Gln | Ser | Thr | Leu | Leu |
| | | 35 | | | | | 40 | | | | | 45 | | | |
| Leu | Pro | Gln | Thr | Gly | Pro | Gly | Leu | Thr | Ser | Gln | Ala | Val | Gly | Arg | Pro |
| | 50 | | | | | 55 | | | | | 60 | | | | |
| Gly | Leu | Ser | Gly | Ser | Ser | Leu | Glu | Pro | His | Leu | Glu | Ala | Ser | Gln | His |
| 65 | | | | | 70 | | | | | 75 | | | | | 80 |

5,484,732

| | | | | | | | | | | | | | | |
|---|---|---|---|---|---|---|---|---|---|---|---|---|---|---|
| Leu | Pro | Gly | Pro | Lys<br>85 | His | Leu | Pro | Gly | Pro<br>90 | Gly | Asn | Asp | Glu<br>95 | Pro |
| Thr | Asp | Leu | Glu<br>100 | Glu | Leu | Glu | Lys | Phe<br>105 | Ala | Lys | Thr | Phe<br>110 | Lys | Gln | Arg |
| Arg | Ile | Lys<br>115 | Leu | Gly | Phe | Thr | Gln<br>120 | Gly | Asp | Val | Gly | Leu<br>125 | Ala | Met | Gly |
| Lys | Leu<br>130 | Tyr | Gly | Asn | Asp | Phe<br>135 | Ser | Gln | Thr | Thr | Ile<br>140 | Ser | Arg | Phe | Glu |
| Ala<br>145 | Leu | Asn | Leu | Ser | Phe<br>150 | Lys | Asn | Met | Cys | Lys<br>155 | Leu | Lys | Pro | Leu | Leu<br>160 |
| Glu | Lys | Trp | Leu | Asn<br>165 | Asp | Ala | Glu | Ser | Ser<br>170 | Pro | Ala | Asp | Pro | Ser<br>175 | Ala |
| Ser | Thr | Pro | Ser<br>180 | Ser | Tyr | Pro | Thr | Leu<br>185 | Ser | Glu | Val | Phe | Gly<br>190 | Arg | Lys |
| Arg | Lys | Lys<br>195 | Arg | Thr | Ser | Ile | Glu<br>200 | Thr | Asn | Ile | Arg | Leu<br>205 | Thr | Leu | Glu |
| Lys | Arg<br>210 | Phe | Gln | Asp | Asn | Pro<br>215 | Lys | Pro | Ser | Ser | Glu<br>220 | Glu | Ile | Ser | Met |
| Ile<br>225 | Ala | Glu | Gln | Leu | Ser<br>230 | Met | Glu | Lys | Glu | Val<br>235 | Val | Arg | Val | Trp | Phe<br>240 |
| Cys | Asn | Arg | Arg | Gln<br>245 | Lys | Glu | Lys | Arg | Ile<br>250 | Asn | Cys | Pro | Val | Ala<br>255 | Thr |
| Pro | Val | Lys | Pro<br>260 | Pro | Ile | Tyr | Asn | Ser<br>265 | Arg | Leu | Val | Ser | Pro<br>270 | Ser | Gly |
| Ser | Leu | Gly<br>275 | Ser | Leu | Ser | Val | Pro<br>280 | Pro | Val | His | Ser | Thr<br>285 | Met | Pro | Gly |
| Thr | Val<br>290 | Thr | Ser | Ser | Cys | Ser<br>295 | Pro | Gly | Asn | Asn | Ser<br>300 | Arg | Pro | Ser | Ser |
| Pro<br>305 | Gly | Ser | Gly | Leu | His<br>310 | Ala | Ser | Ser | Pro | Thr<br>315 | Ala | Ser | Gln | Asn | Asn<br>320 |
| Ser | Lys | Ala | Ala | Met<br>325 | Asn | Pro | Ser | Ser | Ala<br>330 | Ala | Phe | Asn | Ser | Ser<br>335 | Gly |
| Ser | Trp | Tyr | Arg<br>340 | Trp | Asn | His | Pro | Ala<br>345 | Tyr | Leu | His | | | | |

( 2 ) INFORMATION FOR SEQ ID NO:3:

( i ) SEQUENCE CHARACTERISTICS:
        ( A ) LENGTH: 2205 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: Skn-1a ( i x ) FEATURE:
        ( A ) NAME/KEY: CDS
        ( B ) LOCATION: 46..1338

( x i ) SEQUENCE DESCRIPTION: SEQ ID NO:3:

```
ATTCGCGGCC  GCTGGGGGGG  CGCTGGCTTT  GGCCCGCTGC  GGAGG ATG GTG AAT           54
                                                      Met Val Asn
                                                       1

CTG GAG CCC ATG CAC ACA GAG ATC AAG ATG AGT GGG GAT GTC GCT GAT           102
Leu Glu Pro Met His Thr Glu Ile Lys Met Ser Gly Asp Val Ala Asp
     5              10                  15
```

| | | | | | | | | | | | | | | | | |
|---|---|---|---|---|---|---|---|---|---|---|---|---|---|---|---|---|
| TCC | ACA | GAT | GCC | CGC | AGC | ACT | TTT | GGT | CAA | GTG | GAG | TCA | GGA | AAT | GAT | 150 |
| Ser | Thr | Asp | Ala | Arg | Ser | Thr | Phe | Gly | Gln | Val | Glu | Ser | Gly | Asn | Asp | |
| 20 | | | | 25 | | | | | 30 | | | | | | 35 | |

| | | | | | | | | | | | | | | | | |
|---|---|---|---|---|---|---|---|---|---|---|---|---|---|---|---|---|
| CGA | AAT | GGC | CTA | GAT | TTC | AAC | AGA | CAG | ATT | AAG | ACA | GAG | GAT | CTG | GGT | 198 |
| Arg | Asn | Gly | Leu | Asp | Phe | Asn | Arg | Gln | Ile | Lys | Thr | Glu | Asp | Leu | Gly | |
| | | | | 40 | | | | | 45 | | | | | 50 | | |

| | | | | | | | | | | | | | | | | |
|---|---|---|---|---|---|---|---|---|---|---|---|---|---|---|---|---|
| GAC | ACT | TTG | CAC | GAG | AGC | CTC | TCC | CAC | AGG | CCA | TGC | CAC | CTG | ACC | GAA | 246 |
| Asp | Thr | Leu | His | Glu | Ser | Leu | Ser | His | Arg | Pro | Cys | His | Leu | Thr | Glu | |
| | | | 55 | | | | | 60 | | | | | 65 | | | |

| | | | | | | | | | | | | | | | | |
|---|---|---|---|---|---|---|---|---|---|---|---|---|---|---|---|---|
| GGG | CCT | ACC | ATG | ATG | CCT | GGA | AAC | CAA | ATG | TCT | GGG | GAC | ATG | GCT | TCT | 294 |
| Gly | Pro | Thr | Met | Met | Pro | Gly | Asn | Gln | Met | Ser | Gly | Asp | Met | Ala | Ser | |
| | | 70 | | | | | 75 | | | | | 80 | | | | |

| | | | | | | | | | | | | | | | | |
|---|---|---|---|---|---|---|---|---|---|---|---|---|---|---|---|---|
| CTC | CAT | CCA | CTT | CAG | CAG | CTT | GTG | CTG | GTC | CCT | GGC | CAC | TTA | CAG | TCT | 342 |
| Leu | His | Pro | Leu | Gln | Gln | Leu | Val | Leu | Val | Pro | Gly | His | Leu | Gln | Ser | |
| | 85 | | | | | 90 | | | | | 95 | | | | | |

| | | | | | | | | | | | | | | | | |
|---|---|---|---|---|---|---|---|---|---|---|---|---|---|---|---|---|
| GTA | TCC | CAG | TTT | CTG | CTT | TCC | CAG | ACC | CCT | CCT | GGG | CAG | CAA | GGT | CTG | 390 |
| Val | Ser | Gln | Phe | Leu | Leu | Ser | Gln | Thr | Pro | Pro | Gly | Gln | Gln | Gly | Leu | |
| 100 | | | | | 105 | | | | | 110 | | | | | 115 | |

| | | | | | | | | | | | | | | | | |
|---|---|---|---|---|---|---|---|---|---|---|---|---|---|---|---|---|
| CAG | CCG | AAT | CTT | CTC | TCC | TTT | CCA | CAG | CAA | CAG | AGC | ACT | CTA | CTC | CTC | 438 |
| Gln | Pro | Asn | Leu | Leu | Ser | Phe | Pro | Gln | Gln | Gln | Ser | Thr | Leu | Leu | Leu | |
| | | | | 120 | | | | | 125 | | | | | 130 | | |

| | | | | | | | | | | | | | | | | |
|---|---|---|---|---|---|---|---|---|---|---|---|---|---|---|---|---|
| CCA | CAG | ACA | GGA | CCT | GGC | CTC | ACC | TCC | CAG | GCA | GTT | GGA | CGC | CCT | GGG | 486 |
| Pro | Gln | Thr | Gly | Pro | Gly | Leu | Thr | Ser | Gln | Ala | Val | Gly | Arg | Pro | Gly | |
| | | | 135 | | | | | 140 | | | | | 145 | | | |

| | | | | | | | | | | | | | | | | |
|---|---|---|---|---|---|---|---|---|---|---|---|---|---|---|---|---|
| CTG | TCA | GGA | TCC | TCT | TTA | GAG | CCC | CAC | CTG | GAA | GCT | TCT | CAA | CAT | CTG | 534 |
| Leu | Ser | Gly | Ser | Ser | Leu | Glu | Pro | His | Leu | Glu | Ala | Ser | Gln | His | Leu | |
| | | 150 | | | | | 155 | | | | | 160 | | | | |

| | | | | | | | | | | | | | | | | |
|---|---|---|---|---|---|---|---|---|---|---|---|---|---|---|---|---|
| CCA | GGG | CCC | AAG | CAT | CTG | CCT | GGC | CCC | GGA | GGG | AAT | GAC | GAA | CCC | ACT | 582 |
| Pro | Gly | Pro | Lys | His | Leu | Pro | Gly | Pro | Gly | Gly | Asn | Asp | Glu | Pro | Thr | |
| | 165 | | | | | 170 | | | | | 175 | | | | | |

| | | | | | | | | | | | | | | | | |
|---|---|---|---|---|---|---|---|---|---|---|---|---|---|---|---|---|
| GAC | CTG | GAG | GAG | CTG | GAG | AAG | TTC | GCC | AAG | ACC | TTC | AAG | CAG | AGG | CGC | 630 |
| Asp | Leu | Glu | Glu | Leu | Glu | Lys | Phe | Ala | Lys | Thr | Phe | Lys | Gln | Arg | Arg | |
| 180 | | | | | 185 | | | | | 190 | | | | | 195 | |

| | | | | | | | | | | | | | | | | |
|---|---|---|---|---|---|---|---|---|---|---|---|---|---|---|---|---|
| ATA | AAG | CTA | GGC | TTC | ACA | CAG | GGG | GAT | GTG | GGA | TTG | GCG | ATG | GGA | AAG | 678 |
| Ile | Lys | Leu | Gly | Phe | Thr | Gln | Gly | Asp | Val | Gly | Leu | Ala | Met | Gly | Lys | |
| | | | | 200 | | | | | 205 | | | | | 210 | | |

| | | | | | | | | | | | | | | | | |
|---|---|---|---|---|---|---|---|---|---|---|---|---|---|---|---|---|
| CTG | TAT | GGT | AAC | GAC | TTC | AGC | CAG | ACT | ACC | ATC | TCG | AGA | TTT | GAG | GCC | 726 |
| Leu | Tyr | Gly | Asn | Asp | Phe | Ser | Gln | Thr | Thr | Ile | Ser | Arg | Phe | Glu | Ala | |
| | | | 215 | | | | | 220 | | | | | 225 | | | |

| | | | | | | | | | | | | | | | | |
|---|---|---|---|---|---|---|---|---|---|---|---|---|---|---|---|---|
| CTC | AAC | CTG | AGT | TTC | AAG | AAC | ATG | TGT | AAA | CTC | AAG | CCA | CTG | CTG | GAG | 774 |
| Leu | Asn | Leu | Ser | Phe | Lys | Asn | Met | Cys | Lys | Leu | Lys | Pro | Leu | Leu | Glu | |
| | | 230 | | | | | 235 | | | | | 240 | | | | |

| | | | | | | | | | | | | | | | | |
|---|---|---|---|---|---|---|---|---|---|---|---|---|---|---|---|---|
| AAG | TGG | CTG | AAT | GAT | GCA | GAG | TCC | TCC | CCG | GCA | GAC | CCT | TCA | GCA | AGC | 822 |
| Lys | Trp | Leu | Asn | Asp | Ala | Glu | Ser | Ser | Pro | Ala | Asp | Pro | Ser | Ala | Ser | |
| | 245 | | | | | 250 | | | | | 255 | | | | | |

| | | | | | | | | | | | | | | | | |
|---|---|---|---|---|---|---|---|---|---|---|---|---|---|---|---|---|
| ACT | CCC | AGC | TCG | TAC | CCC | ACT | CTC | AGC | GAA | GTA | TTT | GGC | AGG | AAG | AGG | 870 |
| Thr | Pro | Ser | Ser | Tyr | Pro | Thr | Leu | Ser | Glu | Val | Phe | Gly | Arg | Lys | Arg | |
| 260 | | | | | 265 | | | | | 270 | | | | | 275 | |

| | | | | | | | | | | | | | | | | |
|---|---|---|---|---|---|---|---|---|---|---|---|---|---|---|---|---|
| AAG | AAA | CGG | ACC | AGC | ATC | GAG | ACC | AAC | ATC | CGC | CTG | ACT | TTG | GAG | AAG | 918 |
| Lys | Lys | Arg | Thr | Ser | Ile | Glu | Thr | Asn | Ile | Arg | Leu | Thr | Leu | Glu | Lys | |
| | | | | 280 | | | | | 285 | | | | | 290 | | |

| | | | | | | | | | | | | | | | | |
|---|---|---|---|---|---|---|---|---|---|---|---|---|---|---|---|---|
| CGA | TTT | CAA | GAT | AAC | CCT | AAA | CCC | AGC | TCG | GAA | GAG | ATT | TCC | ATG | ATT | 966 |
| Arg | Phe | Gln | Asp | Asn | Pro | Lys | Pro | Ser | Ser | Glu | Glu | Ile | Ser | Met | Ile | |
| | | | 295 | | | | | 300 | | | | | 305 | | | |

| | | | | | | | | | | | | | | | | |
|---|---|---|---|---|---|---|---|---|---|---|---|---|---|---|---|---|
| GCG | GAG | CAG | TTG | TCC | ATG | GAG | AAG | GAA | GTG | GTA | AGA | GTC | TGG | TTC | TGC | 1014 |
| Ala | Glu | Gln | Leu | Ser | Met | Glu | Lys | Glu | Val | Val | Arg | Val | Trp | Phe | Cys | |
| | | 310 | | | | | 315 | | | | | 320 | | | | |

| | | | | | | | | | | | | | | | | |
|---|---|---|---|---|---|---|---|---|---|---|---|---|---|---|---|---|
| AAT | CGA | CGC | CAA | AAG | GAG | AAG | AGA | ATC | AAC | TGC | CCT | GTG | GCC | ACA | CCT | 1062 |
| Asn | Arg | Arg | Gln | Lys | Glu | Lys | Arg | Ile | Asn | Cys | Pro | Val | Ala | Thr | Pro | |
| | 325 | | | | | 330 | | | | | 335 | | | | | |

| | | | | | | | | | | | | | | | |
|---|---|---|---|---|---|---|---|---|---|---|---|---|---|---|---|
| GTC | AAG | CCG | CCC | ATC | TAC | AAC | TCC | CGG | CTG | GTC | TCT | CCC | TCA | GGG | TCT | 1110 |
| Val | Lys | Pro | Pro | Ile | Tyr | Asn | Ser | Arg | Leu | Val | Ser | Pro | Ser | Gly | Ser |
| 340 | | | | 345 | | | | | 350 | | | | | 355 |

```
GTC AAG CCG CCC ATC TAC AAC TCC CGG CTG GTC TCT CCC TCA GGG TCT    1110
Val Lys Pro Pro Ile Tyr Asn Ser Arg Leu Val Ser Pro Ser Gly Ser
340             345                 350                 355

CTG GGC TCC CTC TCA GTC CCT CCT GTC CAC AGC ACC ATG CCT GGA ACA    1158
Leu Gly Ser Leu Ser Val Pro Pro Val His Ser Thr Met Pro Gly Thr
            360                 365                 370

GTA ACG TCA TCC TGT TCC CCT GGG AAC AAC AGC AGG CCC TCG TCT CCC    1206
Val Thr Ser Ser Cys Ser Pro Gly Asn Asn Ser Arg Pro Ser Ser Pro
        375                 380                 385

GGC TCA GGA CTC CAT GCC AGC AGC CCC ACG GCA TCT CAA AAT AAC TCC    1254
Gly Ser Gly Leu His Ala Ser Ser Pro Thr Ala Ser Gln Asn Asn Ser
        390                 395                 400

AAA GCA GCA ATG AAC CCC TCC TCC GCC GCC TTT AAC TCC TCA GGG TCA    1302
Lys Ala Ala Met Asn Pro Ser Ser Ala Ala Phe Asn Ser Ser Gly Ser
        405                 410                 415

TGG TAC CGT TGG AAC CAT CCC GCC TAC CTC CAC TGAGACCAAA AACTTCCTCC  1355
Trp Tyr Arg Trp Asn His Pro Ala Tyr Leu His
420             425                 430

CGTTCCACCT GGCCCTGGTT CCCACCAGGA GGAAGAGCGG CCACACCTTC CACGTATGGA  1415

CAGACACTTT GAGACTCGGA GCGGGAGAAA TGGCCGCTGC TGAAGAGCAA ACCCACAATC  1475

TTGCCTTCTC CTGGATCCAG AGCTTCCAGA GAACCAAGAT GTGACCAAAG CGCACACTC   1535

TTGCCTTGGG CTCTTGATCA CCCGCTGGGA GTTTACCGTG CTCACCCGTG ACCGCTTCAT  1595

GCTCACATGA TGGCTCACCT ATTGGAAAGG CATTCTGCCA TTGTTAGTTT TCAGCTCACC  1655

GGTGGGATTC TGGGACAGCC TTTTGCTCGT TGTGCCAAAC TGCAAGAAGG GTAGTTATGG  1715

TTTTGACTCT GACCTCAGCC ACAATCCTGA ACTGATCCAA ATTCTATGAG AAGACTGAAA  1775

TCTCGTGTCT CTACCAAAGC CTTATTTTGT TAAATTAGCA CAGTTTTCTT ACAGCATATC  1835

CATTTTTGCC CAACTTTCTT TTAGAAATTA CTTCCTTTT CTACAACAAA ACCTGTCTAT   1895

CCTTAGGTCC TACAAAGTCC CTTCCTCTCT ATAAATGGCT AAGCTCCCCT CTGGCCATGT  1955

TGCTCCATTC ACGTGTACTC TTTTGTTGCC CACATGTTCC CAAGTTCAAG AACACTTGTT  2015

TTTTTTCTGT TCTCTGTGGG TTTTCTTGTC CTGTCCCCTC TCCTTGCTCC TGGCCACAGA  2075

GAAGTACACA CACTGTGGCC ACTTTCTTGT ACATAGTCCT TTCCTACTCT GCACTATGAC  2135

CGTTCATCTT TAATGTGTAA TTTCCCAGCG AAATGTTTAA CTCAGGTGTG CATTTTGAAA  2195

AAAAAAAAA                                                          2205
```

( 2 ) INFORMATION FOR SEQ ID NO:4:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Val Asn Leu Glu Pro Met His Thr Glu Ile Lys Met Ser Gly Asp
 1               5                  10                  15

Val Ala Asp Ser Thr Asp Ala Arg Ser Thr Phe Gly Gln Val Glu Ser
                20                  25                  30

Gly Asn Asp Arg Asn Gly Leu Asp Phe Asn Arg Gln Ile Lys Thr Glu
                35                  40                  45

Asp Leu Gly Asp Thr Leu His Glu Ser Leu Ser His Arg Pro Cys His
        50                  55                  60
```

| | | | | | | | | | | | | | | | |
|---|---|---|---|---|---|---|---|---|---|---|---|---|---|---|---|
| Leu | Thr | Glu | Gly | Pro | Thr | Met | Met | Pro | Gly | Asn | Gln | Met | Ser | Gly | Asp |
| 65 | | | | | 70 | | | | | 75 | | | | | 80 |
| Met | Ala | Ser | Leu | His | Pro | Leu | Gln | Gln | Leu | Val | Leu | Val | Pro | Gly | His |
| | | | | 85 | | | | | 90 | | | | | 95 | |
| Leu | Gln | Ser | Val | Ser | Gln | Phe | Leu | Leu | Ser | Gln | Thr | Pro | Pro | Gly | Gln |
| | | | 100 | | | | | 105 | | | | | 110 | | |
| Gln | Gly | Leu | Gln | Pro | Asn | Leu | Leu | Ser | Phe | Pro | Gln | Gln | Ser | Thr | |
| | | 115 | | | | | 120 | | | | | 125 | | | |
| Leu | Leu | Leu | Pro | Gln | Thr | Gly | Pro | Gly | Leu | Thr | Ser | Gln | Ala | Val | Gly |
| | 130 | | | | | 135 | | | | | 140 | | | | |
| Arg | Pro | Gly | Leu | Ser | Gly | Ser | Ser | Leu | Glu | Pro | His | Leu | Glu | Ala | Ser |
| 145 | | | | | 150 | | | | | 155 | | | | | 160 |
| Gln | His | Leu | Pro | Gly | Pro | Lys | His | Leu | Pro | Gly | Pro | Gly | Gly | Asn | Asp |
| | | | | 165 | | | | | 170 | | | | | 175 | |
| Glu | Pro | Thr | Asp | Leu | Glu | Glu | Leu | Glu | Lys | Phe | Ala | Lys | Thr | Phe | Lys |
| | | | 180 | | | | | 185 | | | | | 190 | | |
| Gln | Arg | Arg | Ile | Lys | Leu | Gly | Phe | Thr | Gln | Gly | Asp | Val | Gly | Leu | Ala |
| | | 195 | | | | | 200 | | | | | 205 | | | |
| Met | Gly | Lys | Leu | Tyr | Gly | Asn | Asp | Phe | Ser | Gln | Thr | Thr | Ile | Ser | Arg |
| | 210 | | | | | 215 | | | | | 220 | | | | |
| Phe | Glu | Ala | Leu | Asn | Leu | Ser | Phe | Lys | Asn | Met | Cys | Lys | Leu | Lys | Pro |
| 225 | | | | | 230 | | | | | 235 | | | | | 240 |
| Leu | Leu | Glu | Lys | Trp | Leu | Asn | Asp | Ala | Glu | Ser | Ser | Pro | Ala | Asp | Pro |
| | | | | 245 | | | | | 250 | | | | | 255 | |
| Ser | Ala | Ser | Thr | Pro | Ser | Ser | Tyr | Pro | Thr | Leu | Ser | Glu | Val | Phe | Gly |
| | | | 260 | | | | | 265 | | | | | 270 | | |
| Arg | Lys | Arg | Lys | Lys | Arg | Thr | Ser | Ile | Glu | Thr | Asn | Ile | Arg | Leu | Thr |
| | | 275 | | | | | 280 | | | | | 285 | | | |
| Leu | Glu | Lys | Arg | Phe | Gln | Asp | Asn | Pro | Lys | Pro | Ser | Ser | Glu | Glu | Ile |
| | 290 | | | | | 295 | | | | | 300 | | | | |
| Ser | Met | Ile | Ala | Glu | Gln | Leu | Ser | Met | Glu | Lys | Glu | Val | Val | Arg | Val |
| 305 | | | | | 310 | | | | | 315 | | | | | 320 |
| Trp | Phe | Cys | Asn | Arg | Arg | Gln | Lys | Glu | Lys | Arg | Ile | Asn | Cys | Pro | Val |
| | | | | 325 | | | | | 330 | | | | | 335 | |
| Ala | Thr | Pro | Val | Lys | Pro | Pro | Ile | Tyr | Asn | Ser | Arg | Leu | Val | Ser | Pro |
| | | | 340 | | | | | 345 | | | | | 350 | | |
| Ser | Gly | Ser | Leu | Gly | Ser | Leu | Ser | Val | Pro | Pro | Val | His | Ser | Thr | Met |
| | | 355 | | | | | 360 | | | | | 365 | | | |
| Pro | Gly | Thr | Val | Thr | Ser | Ser | Cys | Ser | Pro | Gly | Asn | Asn | Ser | Arg | Pro |
| | 370 | | | | | 375 | | | | | 380 | | | | |
| Ser | Ser | Pro | Gly | Ser | Gly | Leu | His | Ala | Ser | Ser | Pro | Thr | Ala | Ser | Gln |
| 385 | | | | | 390 | | | | | 395 | | | | | 400 |
| Asn | Asn | Ser | Lys | Ala | Ala | Met | Asn | Pro | Ser | Ser | Ala | Ala | Phe | Asn | Ser |
| | | | | 405 | | | | | 410 | | | | | 415 | |
| Ser | Gly | Ser | Trp | Tyr | Arg | Trp | Asn | His | Pro | Ala | Tyr | Leu | His | | |
| | | | 420 | | | | | 425 | | | | | 430 | | |